United States Patent
Arimitsu

(10) Patent No.: US 11,873,380 B2
(45) Date of Patent: Jan. 16, 2024

(54) PHOTOREACTIVE COMPOSITION, REACTION PRODUCT, AND METHOD OF PRODUCING REACTION PRODUCT

(71) Applicant: Tokyo University of Science Foundation, Tokyo (JP)

(72) Inventor: Koji Arimitsu, Tokyo (JP)

(73) Assignee: Tokyo University of Science Foundation, Tokyo (JP)

( * ) Notice: Subject to any disclaimer, the term of this patent is extended or adjusted under 35 U.S.C. 154(b) by 721 days.

(21) Appl. No.: 17/053,431

(22) PCT Filed: May 7, 2019

(86) PCT No.: PCT/JP2019/018289
§ 371 (c)(1),
(2) Date: Nov. 6, 2020

(87) PCT Pub. No.: WO2019/216321
PCT Pub. Date: Nov. 14, 2019

(65) Prior Publication Data
US 2021/0253826 A1    Aug. 19, 2021

(30) Foreign Application Priority Data

May 7, 2018   (JP) .................................. 2018-089280

(51) Int. Cl.
| | | |
|---|---|---|
| C08K 5/34 | (2006.01) | |
| C08K 5/3435 | (2006.01) | |
| C07D 295/192 | (2006.01) | |
| C07D 307/88 | (2006.01) | |
| C08F 20/32 | (2006.01) | |

(52) U.S. Cl.
CPC ........ *C08K 5/3435* (2013.01); *C07D 295/192* (2013.01); *C07D 307/88* (2013.01); *C08F 20/32* (2013.01)

(58) Field of Classification Search
CPC .. C08K 5/3435; C07D 295/19; C07D 307/88; C08F 20/32; C08F 120/32; C08F 2/50; C08G 59/68; C08L 101/00; C08L 25/06; C08L 33/068
See application file for complete search history.

(56) References Cited

U.S. PATENT DOCUMENTS

| | | | | |
|---|---|---|---|---|
| 4,906,317 A * | 3/1990 | Liu | ............................. | C09J 4/00 |
| | | | | 526/194 |
| 5,565,567 A * | 10/1996 | Share | ................. | C07D 295/192 |
| | | | | 544/391 |
| 6,965,040 B1 * | 11/2005 | Gao | ....................... | C07F 9/2408 |
| | | | | 560/103 |
| 10,941,225 B2 * | 3/2021 | Woods | ..................... | C08F 22/10 |
| 2017/0101521 A1 * | 4/2017 | Koyama | ................. | G03F 7/004 |
| 2019/0002403 A1 * | 1/2019 | Yanaba | ................ | C08G 59/686 |

FOREIGN PATENT DOCUMENTS

JP         2018131593 A         8/2018
WO     WO-2019216322 A1 *   11/2019

OTHER PUBLICATIONS

Nov. 8, 2022 (JP) Office Action Application No. 2020-518304.
Arimitsu et al. "Application to Photoreactive Materials of Photochemical Generation of Superbases with High Eficiency Based on Photodecarboxylation Reactions" Chem Mater. 2013, 25, 4461-4463.
Cameron et al. "Photogeneration of Organic Bases from o-Nitrobenzyl-Derived Carbamates". J. Am. Chem. Soc. 1991, 113, 4303.

* cited by examiner

*Primary Examiner* — Sanza L. McClendon
(74) *Attorney, Agent, or Firm* — Banner & Witcoff, Ltd.

(57) ABSTRACT

A photoreactive composition including a base-reactive compound, a photobase generator that is represented by the following Formula (1) and that generates a base when irradiated with light, and at least one compound selected from the group consisting of a polycyclic aromatic compound having a fused ring structure having two or more rings and a polycyclic aromatic compound having three or more aromatic rings and having a conjugated structure including any two or more of the three or more aromatic rings, in which the base-reactive compound is a compound having two or more groups that will have their polarity converted by the action of a base and that exhibit reactivity, in one molecule, or a compound having two or more groups that will react under the action of a base, in one molecule.

20 Claims, 5 Drawing Sheets

PHOTOREACTIVE COMPOSITION, REACTION PRODUCT, AND METHOD OF PRODUCING REACTION PRODUCT

TECHNICAL FIELD

The present invention relates to a photoreactive composition, a reaction product, and a method of producing a reaction product.

BACKGROUND ART

Photopolymerizable materials to be polymerized when irradiated with light are widely practically used, and hold predominant positions in the fields of, for example, electronic materials or printing materials, because polymerization reactions thereof can be precisely controlled by relatively simple operations.

Photopolymerizable materials which have been heretofore actively studied are, for example, a radical polymerization resin composition containing a photoinitiator that generates radical species by exposure, and a radical-polymerizable monomer or oligomer, and an acid catalyst-based resin composition containing a photoacid generator that generates acid by exposure, and a monomer or oligomer to be polymerized by the action of an acid.

Base catalyst-based photopolymerizable materials are also known as photopolymerizable materials, such a base catalyst-based photopolymerizable material containing a photobase generator that generates base by exposure, and a monomer or oligomer to be polymerized by the action of a base. A photobase generator known is, for example, an ionic photobase generator corresponding to a salt of a strong base such as guanidine and a carboxylic acid (see, for example, Non-Patent Literature 1). Such an ionic photobase generator not only allows a decarboxylation reaction to progress in a carboxy group by exposure, but also generates a base by elimination of a strong base forming a salt together with the carboxy group.

However, such an ionic photobase generator has the problem of being low in stability during storage and low in solubility, although high in reactivity. A resin composition using such an ionic photobase generator also has the problem of being low in stability.

On the contrary, non-ionic photobase generators have also been studied. A non-ionic photobase generator known is, for example, a non-ionic photobase generator that is a carbamate having a nitrobenzyl skeleton, in which a base is generated by not only progression of a decarboxylation reaction by exposure, but also elimination of a primary amine or secondary amine (see, for example, Non-Patent Literature 2). Such a non-ionic photobase generator allows the above problems about ionic photobase generators to be solved.

CITATION LIST

Non-Patent Literature

[Non-Patent Literature 1] K. Arimitsu, R. Endo, Chem. Mater. 2013, 25, 4461-4463.
[Non-Patent Literature 2] J. F. Cameron, J. M. J. Frechet, J. Am. Chem. Soc. 1991, 113, 4303.

SUMMARY OF INVENTION

Technical Problem

However, the non-ionic photobase generator disclosed in Non-Patent Literature 2 is weak in basicity, and thus a resin composition using such a non-ionic photobase generator still has room for improvement in terms of an enhancement in polymerization reactivity. There is also room for improvement in optical sensitivity of a photobase generator in the long-wavelength ultraviolet region because a conventional resin composition has been low in generating efficiency of a base in irradiation with light in the long-wavelength ultraviolet region.

An object of the invention is to provide a photoreactive composition excellent in optical sensitivity of a photobase generator in the long-wavelength ultraviolet region, a reaction product obtained by reacting the photoreactive composition, and a method of producing a reaction product by use of the photoreactive composition.

Solution to Problem

Examples of means for solving the above problem are shown below.

<1> A photoreactive composition, comprising:

a base-reactive compound;

a photobase generator that is represented by the following Formula (1) and that generates a base when irradiated with light; and at least one compound selected from the group consisting of a polycyclic aromatic compound having a fused ring structure having two or more rings, and a polycyclic aromatic compound having three or more aromatic rings and having a conjugated structure including any two or more of the three or more aromatic rings, wherein the base-reactive compound is a compound having two or more groups that will have their polarity converted by the action of a base and that exhibit reactivity, in one molecule, or a compound having two or more groups that will react under the action of a base, in one molecule.

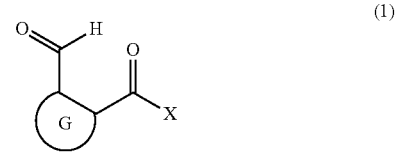

(1)

In Formula (1), G is a divalent aromatic group; and X is a group represented by the following Formula (1)-11, (1)-12, (1)-13, (1)-14, or (1)-15.

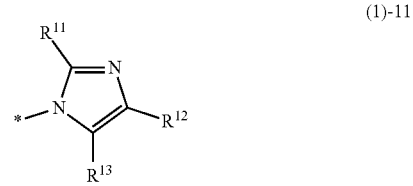

(1)-11

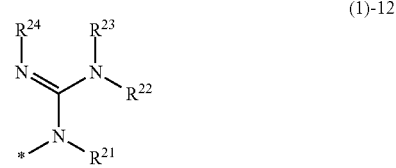

(1)-12

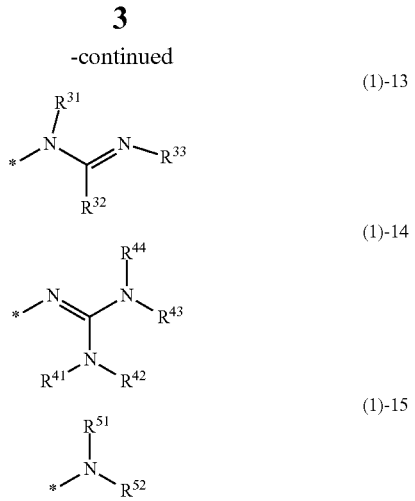

In Formula (1)-11 to Formula (1)-15, each of $R^{11}$, $R^{12}$, $R^{13}$, $R^{22}$, $R^{23}$, $R^{24}$, $R^{32}$, $R^{33}$, $R^{41}$, $R^{42}$, $R^{43}$, and $R^{44}$ independently represents a hydrogen atom or a hydrocarbon group; each of $R^{21}$, $R^{31}$, $R^{51}$, and $R^{52}$ independently represents a hydrocarbon group; in a case in which two or more of $R^{11}$, $R^{12}$, and $R^{13}$ are hydrocarbon groups, these hydrocarbon groups are optionally bound to each other to form a ring; in a case in which two or more of $R^{21}$, $R^{22}$, $R^{23}$, and $R^{24}$ are hydrocarbon groups, these hydrocarbon groups are optionally bound to each other to form a ring; in a case in which two or more of $R^{31}$, $R^{32}$, and $R^{33}$ are hydrocarbon groups, these hydrocarbon groups are optionally bound to each other to form a ring; in a case in which two or more of $R^{41}$, $R^{42}$, $R^{43}$, and $R^{44}$ are hydrocarbon groups, these hydrocarbon groups are optionally bound to each other to form a ring; $R^{51}$ and $R^{52}$ are optionally bound to each other to form a ring; and a bond marked with a symbol * is formed toward a carbon atom to which X is bound.

<2> The photoreactive composition according to <1>, wherein the polycyclic aromatic compound having a fused ring structure having two or more rings has three or more ring structures.

<3> The photoreactive composition according to <1> or <2>, wherein the polycyclic aromatic compound having a fused ring structure having two or more rings is at least one selected from the group consisting of anthraquinone, thioxanthone, anthracene, and any derivative thereof.

<5> The photoreactive composition according to any one of <1> to <3>, wherein:
the polycyclic aromatic compound having three or more aromatic rings and having a conjugated structure including any two or more of the three or more aromatic rings is a benzophenone derivative, and
the benzophenone derivative is a compound in which at least one carbon atom included in an aromatic ring in a benzophenone skeleton is bound to the aromatic ring directly or via a divalent linking group.

<5> A reaction product obtained by reacting the photoreactive composition according to any one of <1> to <4>.

<6> A method of producing a reaction product, the method comprising:
a step of irradiating the photoreactive composition according to any one of <1> to <4> with light, thereby generating the base from the photobase generator.

<7> The method of producing a reaction product according to <6>, wherein the photoreactive composition is irradiated with light at a wavelength of 300 nm or more.

Advantageous Effects of Invention

The invention can provide a photoreactive composition excellent in optical sensitivity of a photobase generator in the long-wavelength ultraviolet region, a reaction product obtained by reacting the photoreactive composition, and a method of producing a reaction product by use of the photoreactive composition.

DESCRIPTION OF EMBODIMENTS

Figure 1:
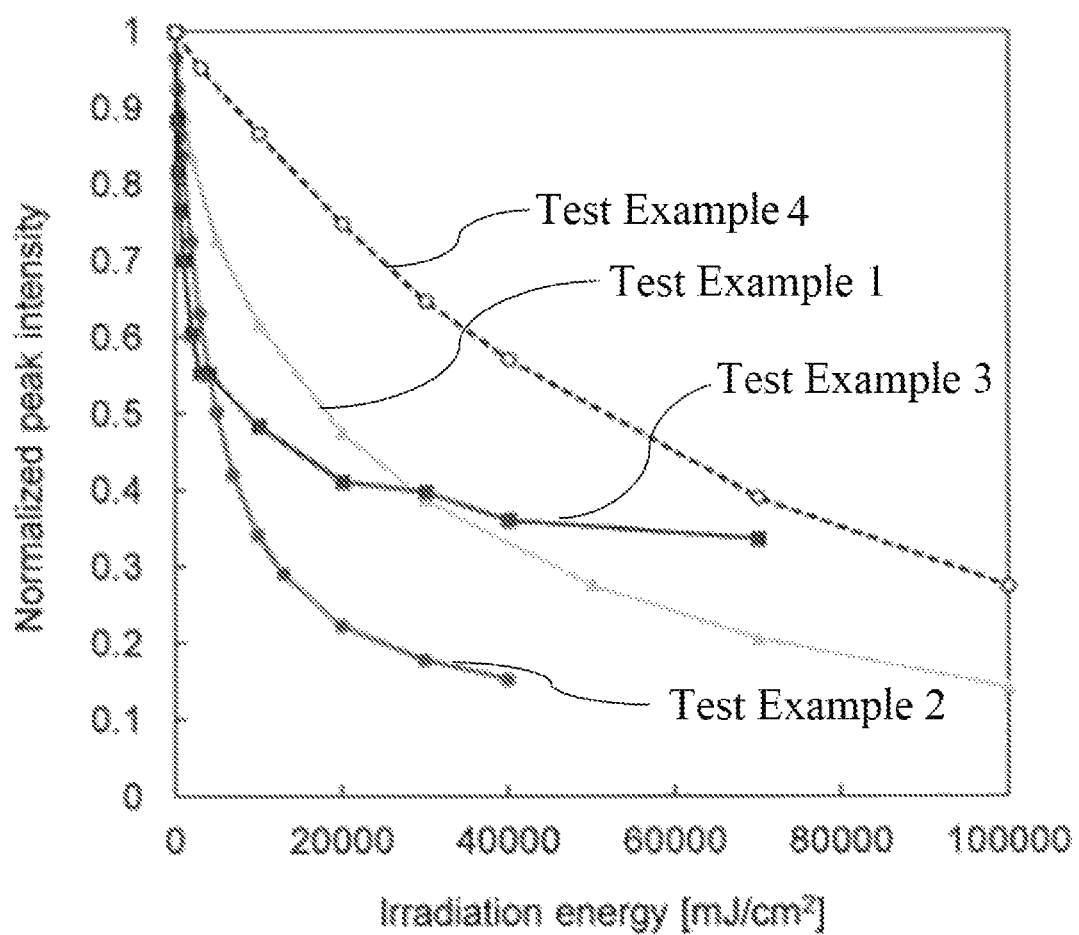
FIG. 1 is a graph illustrating the peak intensity derived from the stretching vibration of C=O of an amide group in a compound (1)-5B-101 in Test Examples 1 to 4.

A numerical value range herein represented by "(from) . . . to . . . " means that numerical values described before and after "to" are encompassed as the lower limit and the upper limit, respectively.

[Photoreactive Composition]

The photoreactive composition of the present disclosure includes a base-reactive compound, a photobase generator that is represented by the following Formula (1) and that generates a base when irradiated with light, and at least one compound selected from the group consisting of a polycyclic aromatic compound having a fused ring structure having two or more rings and a polycyclic aromatic compound having three or more aromatic rings and having a conjugated structure including any two or more of the three or more aromatic rings, wherein the base-reactive compound is a compound having two or more groups that will have their polarity converted by the action of a base and that exhibit reactivity, in one molecule, or a compound having two or more groups that will react under the action of a base, in one molecule.

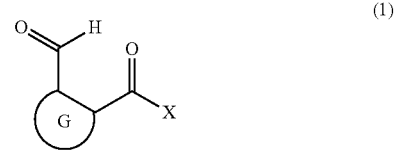

In Formula (1), G is a divalent aromatic group; and X is a group represented by the following Formula (1)-11, (1)-12, (1)-13, (1)-14, or (1)-15.

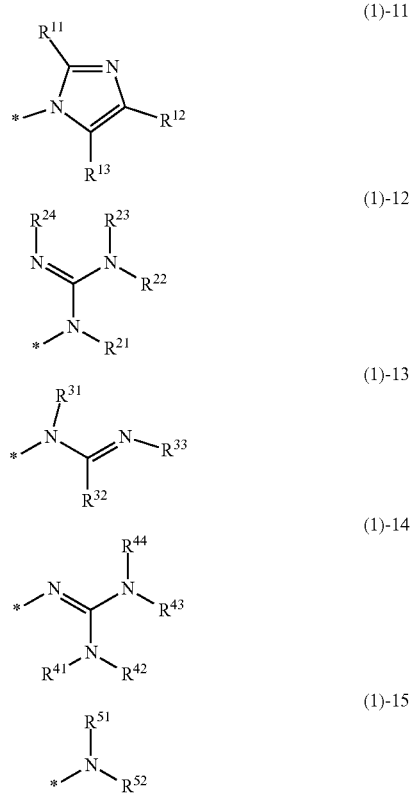

In Formula (1)-11 to Formula (1)-15, $R^{11}$, $R^{12}$, $R^{13}$, $R^{22}$, $R^{23}$, $R^{24}$, $R^{32}$, $R^{33}$, $R^{41}$, $R^{42}$, $R^{43}$, and $R^{44}$ are each independently a hydrogen atom or a hydrocarbon group; $R^{21}$, $R^{31}$, $R^{51}$, and $R^{52}$ are each independently a hydrocarbon group; in a case in which two or more of $R^{11}$, $R^{12}$, and $R^{13}$ are hydrocarbon groups, these hydrocarbon groups are optionally bound to each other to form a ring, in a case in which two or more of $R^{21}$, $R^{22}$, $R^{23}$, and $R^{24}$ are hydrocarbon groups, these hydrocarbon groups are optionally bound to each other to form a ring, in a case in which two or more of $R^{31}$, $R^{32}$, and $R^{33}$ are hydrocarbon groups, these hydrocarbon groups are optionally bound to each other to form a ring, in a case in which two or more of $R^{41}$, $R^{42}$, $R^{43}$, and $R^{44}$ are hydrocarbon groups, these hydrocarbon groups are optionally bound to each other to form a ring, and $R^{51}$ and $R^{52}$ are optionally bound to each other to form a ring; and a bond marked with a symbol * is formed toward a carbon atom to which X is bound.

A photoreactive composition containing a photobase generator has not been sometimes sufficient in photosensitivity in the long-wavelength ultraviolet region, and has been required to generate a base by isomerization (cyclization) of the photobase generator due to irradiation with light in the short-wavelength ultraviolet region from a radiation source such as a 254-nm mercury lamp.

In this regard, the photoreactive composition in the disclosure includes a photobase generator, and at least one compound (herein, sometimes referred to as "specified polycyclic aromatic compound") selected from the group consisting of a polycyclic aromatic compound having a fused ring structure having two or more rings (herein, sometimes referred to as "first polycyclic aromatic compound") and a polycyclic aromatic compound having three or more aromatic rings and having a conjugated structure including any two or more of the three or more aromatic rings (herein, sometimes referred to as "second polycyclic aromatic compound"), and thus is excellent in optical sensitivity of the photobase generator in the long-wavelength ultraviolet region. For example, the photoreactive composition in the disclosure easily generates a base by isomerization (cyclization) of the photobase generator in irradiation with light in the long-wavelength ultraviolet region, as compared with a case in which the specified polycyclic aromatic compound is not contained. The photoreactive composition in the disclosure is thus excellent in optical sensitivity of the photobase generator, for example, in a long-wavelength ultraviolet region of 300 nm or more, and more specifically is excellent in optical sensitivity to i beam (365 nm) or an active energy line at a longer wavelength and can be applied in a wider range.

For example, the photoreactive composition in the disclosure is used for production of a reaction product by light irradiation. Specifically, the photoreactive composition is irradiated with light to generate a base from the photobase generator, thereby allowing a functional group, included in the base-reactive compound, that will have the polarity converted by the action of the base generated and that exhibit reactivity, or allowing a functional group included in the base-reactive compound that will react under the action of the base generated. Thus, the photoreactive composition is irradiated with light to generate a base, thereby allowing the base-reactive compound included in the photoreactive composition to be reacted, thereby providing a reaction product.

The photoreactive composition in the disclosure may be a photocurable composition that is to be cured by a reaction of the base-reactive compound by light irradiation, and such a photocurable composition may be used for production of a cured product by light irradiation.

The photoreactive composition in the disclosure may be a photoreactive material (positive type) to be solubilized by light irradiation, or may be a photoreactive material (negative type) to be cured by light irradiation.

(Base-Reactive Compound)

The photoreactive composition in the disclosure includes a base-reactive compound. The base-reactive compound is a compound (herein, sometimes referred to as "base-reactive compound (9-2a)") having two or more groups that will have their polarity converted by the action of a base and that exhibit reactivity, in one molecule, or a compound (herein, sometimes referred to as "base-reactive compound (9-2b)") having two or more groups that will react under the action of a base, in one molecule. The base-reactive compound (9-2b) is different from the base-reactive compound (9-2a) in that such groups to be reacted will not have their polarity converted by the action of a base.

Examples of the reaction that progresses in the base-reactive compound include addition polymerization and condensation polymerization.

The base-reactive compound may be any of a monomer, an oligomer, or a polymer, and may be any of a low-molecular-weight compound or a high-molecular-weight compound.

The base-reactive compound here used can be any known base-reactive compound, for example, a base-reactive compound described in "Japanese Patent Application Laid-Open (JP-A) No. 2011-80032", provided that such a base-reactive compound is merely one example.

Examples of the base-reactive compound (9-2a) include a compound that is to be decomposed by the action of a base and thus changed in polarity, thereby exhibiting reactivity. Examples of the base-reactive compound (9-2a) include a compound having a carbonate skeleton (—O—C(=O)—O—), and a photosensitive polyimide.

Examples of the base-reactive compound (9-2b) include an epoxy resin, a (meth)acrylate resin, and a silicone resin.

Herein, "(meth)acrylate" represents a concept encompassing both "acrylate" and "methacrylate".

The base-reactive compound included in the photoreactive composition in the disclosure may be adopted singly, or in combination of two or more kinds thereof, and in a case of two or more kinds, the combination and the ratio can be arbitrarily set.

(Photobase Generator)

The photoreactive composition in the disclosure includes a photobase generator (herein, sometimes referred to as "compound (1)") that is represented by Formula (1) and that generates a base when irradiated with light.

The compound (1) is a compound that is represented by Formula (1) and that has a carboxylic acid amide bond formed by binding a nitrogen atom in X to a carbon atom in a carbonyl group.

The compound (1) generates a compound (herein, sometimes referred to as "compound (1')") represented by the following Formula (1'), namely, a base according to a tertiary amine, by progression of a cyclization reaction so that a formyl group and an amide bond disappear when irradiated with light, as represented by the following Formula (i). The "base according to a tertiary amine" means a base having a structure in which no hydrogen atom is directly bound to a nitrogen atom in X bound to a carbon atom in a carbonyl group. The compound (1) has the common property of generating the base according to a tertiary amine when irradiated with light.

The photobase generator being the compound (1) is a non-ionic photobase generator, and is high in stability during storage and also high in solubility unlike a conventional ionic photobase generator, and a photoreactive composition using the photobase generator is high in stability.

A conventional non-ionic photobase generator has been configured to generate a primary amine or secondary amine as a base when irradiated with light, and such a base has been weak in basicity and thus a photoreactive composition using such a conventional non-ionic photobase generator has been insufficient in reactivity during light irradiation. On the contrary, the photobase generator being the compound (1) generates a base according to a tertiary amine not corresponding to any primary amine or secondary amine, as a base, as described above, and a photoreactive composition using the photobase generator is favorable in reactivity during light irradiation.

In Formula (1), G is a divalent aromatic group, and a formyl group (—C(=O)—H) and —C(=O)—X are bound.

The respective binding positions of a formyl group and —C(=O)—X to G are in an ortho-position. In other words, an atom to which a formyl group is bound and an atom to which —C(=O)—X is bound, among atoms included in a ring skeleton of are adjacent (directly bound) to each other in the ring skeleton of G.

The aromatic group in G may be any of a divalent aromatic hydrocarbon group or a divalent aromatic heterocyclic group, or may be a divalent group (herein, such a group is regarded as an aromatic heterocyclic group) obtained by ring fusion of an aromatic hydrocarbon group and an aromatic heterocyclic group.

The aromatic hydrocarbon group and the aromatic heterocyclic group may each have a substituent.

The "aromatic hydrocarbon group having a substituent" means that one or more hydrogen atoms included in the aromatic hydrocarbon group is substituted with any group (substituent) other than a hydrogen atom.

The "aromatic heterocyclic group having a substituent" means that one or more hydrogen atoms included in the aromatic heterocyclic group is substituted with any group (substituent) other than a hydrogen atom.

The aromatic group in G may be either monocyclic or polycyclic, and the number of atoms (number of ring members) included in the ring skeleton is not particularly limited, and is preferably from 3 to 20.

Examples of the aromatic hydrocarbon group as the aromatic group in G include a 1,2-phenylene group, a naphthalene-1,2-diyl group, a naphthalene-2,3-diyl group, a toluene-2,3-diyl group, a toluene-3,4-diyl group, an o-xylene-3,4-diyl group, an o-xylene-4,5-diyl group, an m-xylene-4,5-diyl group, a p-xylene-2,3-diyl group, an anthracene-1,2-diyl group, and an anthracene-2,3-diyl group. One or more hydrogen atoms in the aromatic hydrocarbon group may be each substituted with a substituent, for example, the aromatic hydrocarbon group or alkyl group exemplified. The aromatic hydrocarbon group having such a substituent preferably has from 6 to 20 carbon atoms also including carbon atom(s) of the substituent.

The alkyl group (hereinafter, sometimes referred to as "substituent alkyl group") with which one or more hydrogen atoms of the aromatic hydrocarbon group exemplified are/is substituted may be any of a linear, branched, or cyclic alkyl group, and may be any of a monocyclic or polycyclic alkyl group in a case in which the alkyl group is a cyclic alkyl group. The substituent alkyl group preferably has from 1 to 10 carbon atoms.

The linear or branched substituent alkyl group preferably has from 1 to 10 carbon atoms, and examples include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a 1-methylbutyl group, a n-hexyl group, a 2-methylpentyl group, a 3-methylpentyl group, a 2,2-dimethylbutyl group, a 2,3-dimethylbutyl group, a n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, a n-octyl group, an isooctyl group, a 2-ethylhexyl group, a nonyl group, and a decyl group.

The cyclic substituent alkyl group preferably has from 3 to 10 carbon atoms, and examples thereof include a cyclopropyl group, a cyclobutyl group, a cyclopentyl group, a cyclohexyl group, a cycloheptyl group, a cyclooctyl group,

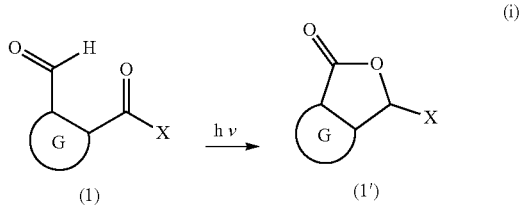

a cyclononyl group, a cyclodecyl group, a norbornyl group, an isobornyl group, a 1-adamantyl group, a 2-adamantyl group, and a tricyclodecyl group, and further include such a cyclic alkyl group in which one or more hydrogen atoms are/is substituted with a linear, branched, or cyclic alkyl group. Examples of the linear, branched, or cyclic alkyl group with which hydrogen atom(s) are/is substituted include the same as in the substituent alkyl group.

Examples of the aromatic heterocyclic group as the aromatic group in G include a group obtained by removing two hydrogen atoms each bound to a carbon atom or a hetero atom included in the ring skeleton, from such each aromatic heterocyclic compound.

Preferable examples of the aromatic heterocyclic compound include a compound having one or more sulfur atoms as atom(s) included in the aromatic heterocyclic skeleton (sulfur-containing aromatic heterocyclic compound), a compound having one or more nitrogen atoms as atom(s) included in the aromatic heterocyclic skeleton (nitrogen-containing aromatic heterocyclic compound), a compound having one or more oxygen atoms as atom(s) included in the aromatic heterocyclic skeleton (oxygen-containing aromatic heterocyclic compound), and a compound having two hetero atoms different from each other, selected from the group consisting of a sulfur atom, a nitrogen atom, and an oxygen atom, as atoms included in the aromatic heterocyclic skeleton.

Examples of the sulfur-containing aromatic heterocyclic compound include thiophene and benzothiophene.

Examples of the nitrogen-containing aromatic heterocyclic compound include pyrrole, imidazole, pyrazole, pyridine, pyrazine, pyrimidine, pyridazine, triazine, indole, isoindole, benzimidazole, purine, indazole, quinoline, isoquinoline, quinoxaline, quinazoline, and cinnoline.

Examples of the oxygen-containing aromatic heterocyclic compound include furan, benzofuran (1-benzofuran), and isobenzofuran (2-benzofuran).

Examples of the compound having two hetero atoms different from each other, included in the aromatic heterocyclic skeleton, include oxazole, isoxazole, thiazole, benzoxazole, benzisoxazole, and benzothiazole.

The atom to which a formyl group is bound and the atom to which —C(=O)—X is bound, among atoms included in the ring skeleton of the aromatic heterocyclic group, may be each a carbon atom or a hetero atom, and are preferably each a carbon atom.

The number of hetero atom(s) included in the ring skeleton in the aromatic heterocyclic group is preferably from 1 to 3, and more preferably 1 or 2.

In a case in which the number of hetero atom(s) included in the ring skeleton in the aromatic heterocyclic group is two or more, such hetero atoms may be all the same, may be all different, or may be only partially the same.

Examples of the substituent in the aromatic hydrocarbon group or aromatic heterocyclic group in G include the substituent alkyl group, an alkoxy group, an aryloxy group, a dialkylamino group, a diarylamino group, an alkylarylamino group, an alkylcarbonyl group, an arylcarbonyl group, an alkyloxycarbonyl group, an aryloxycarbonyl group, an alkylcarbonyloxy group, an arylcarbonyloxy group, an alkylthio group, an arylthio group, a cyano group (—CN), a halogen atom, a nitro group, a haloalkyl group (alkyl halide group), a hydroxyl group (—OH), a mercapto group (—SH), the aromatic hydrocarbon group, and the aromatic heterocyclic group.

The number of such substituent(s) in the aromatic hydrocarbon group or aromatic heterocyclic group in G may be only one, or two or more, and all hydrogen atoms may be each substituted with the substituent. The number of such substituent(s) is, for example, preferably from 1 to 4, more preferably from 1 to 3, and still more preferably 1 or 2, depending on the number of hydrogen atoms that can be substituted.

In a case in which the number of such substituents in the aromatic hydrocarbon group or aromatic heterocyclic group is two or more, such substituents may be all the same, may be all different, or may be only partially the same.

Examples of the alkoxy group as the substituent include a monovalent group obtained by binding the substituent alkyl group to an oxygen atom, for example, a methoxy group, an ethoxy group, a n-propoxy group, an isopropoxy group, or a cyclopropoxy group.

The aryl group bound to an oxygen atom in the aryloxy group as the substituent may be any of a monocyclic or polycyclic aryl group, and preferably has from 6 to 10 carbon atoms. Examples of such an aryl group include a phenyl group, a 1-naphthyl group, a 2-naphthyl group, an o-tolyl group, a m-tolyl group, a p-tolyl group, and a xylyl group (dimethylphenyl group), and further include such an aryl group in which one or more hydrogen atoms are/is substituted with, for example, such an aryl group or the substituent alkyl group. The aryl group having such a substituent preferably has from 6 to 10 carbon atoms also including carbon atom(s) of the substituent.

Examples of the dialkylamino group as the substituent include a monovalent group obtained by substituting each of two hydrogen atoms in an amino group (—NH$_2$) such as a dimethylamino group or a methylethylamino group with the substituent alkyl group. Such two alkyl groups bound to a nitrogen atom in the dialkylamino group may be the same as or different from each other.

Examples of the diarylamino group as the substituent include a monovalent group obtained by substituting each of two hydrogen atoms in an amino group such as a diphenylamino group or a phenyl-1-naphthylamino group with the aryl group. Such aryl groups bound to a nitrogen atom in the diarylamino group may be the same as or different from each other.

Examples of the alkylarylamino group as the substituent include a monovalent group obtained by substituting one hydrogen atom of two hydrogen atoms in an amino group such as a methylphenylamino group, with the substituent alkyl group, and substituting another hydrogen atom thereof with the aryl group.

Examples of the alkylcarbonyl group as the substituent include a monovalent group obtained by binding the substituent alkyl group to a carbonyl group (—C(=O)—), for example, a methylcarbonyl group (acetyl group).

Examples of the arylcarbonyl group as the substituent include a monovalent group obtained by binding the aryl group to a carbonyl group, for example, a phenylcarbonyl group (benzoyl group).

Examples of the alkyloxycarbonyl group as the substituent include a monovalent group obtained by binding the alkoxy group to a carbonyl group, for example, a methyloxycarbonyl group (methoxycarbonyl group).

Examples of the aryloxycarbonyl group as the substituent include a monovalent group obtained by binding the aryloxy group to a carbonyl group, for example, a phenyloxycarbonyl group (phenoxycarbonyl group).

Examples of the alkylcarbonyloxy group as the substituent include a monovalent group obtained by binding the substituent alkyl group to a carbon atom of a carbonyloxy group (—C(=O)—O—), for example, a methylcarbonyloxy group.

Examples of the arylcarbonyloxy group as the substituent include a monovalent group obtained by binding the aryl group to a carbon atom of a carbonyloxy group, for example, a phenylcarbonyloxy group.

Examples of the alkylthio group as the substituent include a monovalent group obtained by binding the substituent alkyl group to a sulfur atom, for example, a methylthio group, an ethylthio group, a n-propylthio group, an isopropylthio group, or a cyclopropylthio group.

Examples of the arylthio group as the substituent include a monovalent group obtained by binding the aryl group to a sulfur atom, for example, a phenylthio group, a 1-naphthylthio group, or a 2-naphthylthio group.

Examples of the halogen atom as the substituent include a fluorine atom (—F), a chlorine atom (—Cl), a bromine atom (—Br), and an iodine atom (—I).

Examples of the haloalkyl group as the substituent include a group obtained by substituting one or more hydrogen atoms of the substituent alkyl group with halogen atom(s).

Examples of each halogen atom in the haloalkyl group include those described above, exemplified as halogen atoms serving as substituents.

The number of halogen atom(s) in the haloalkyl group is not particularly limited, and may be one, or two or more. In a case in which the number of halogen atom(s) in the haloalkyl group is two or more, such a plurality of halogen atoms may be all the same, may be all different, or may be only partially the same. The haloalkyl group may be a perhaloalkyl group in which all hydrogen atoms in the alkyl group are each substituted with a halogen atom.

The haloalkyl group is not particularly limited, and examples thereof include a chloromethyl group, a dichloromethyl group, a trichloromethyl group, and a trifluoromethyl group.

In a case in which the substituent in the aromatic hydrocarbon group or aromatic heterocyclic group in G is, for example, an electron-donating group such as an alkoxy group, an aryloxy group, a dialkylamino group, a diarylamino group, an alkylarylamino group, an alkylthio group, or an arylthio group, the compound (1) is longer in wavelength of light necessary for generation of a base by light irradiation (increased in wavelength). In other words, the substituent as such an electron-donating group has the advantage of enabling the compound (1) to be increased in wavelength of light necessary for generation of a base.

The position of the substituent in the aromatic hydrocarbon group or aromatic heterocyclic group is not particularly limited.

G is preferably an aromatic hydrocarbon group optionally having a substituent, such a substituent is more preferably an aromatic hydrocarbon group optionally having one or more in total of one or more kinds selected from the group consisting of an alkoxy group, an aryloxy group, a dialkylamino group, a diarylamino group, an alkylarylamino group, an alkylthio group, and an arylthio group, and examples of such G include a group represented by the following Formula (1)-21.

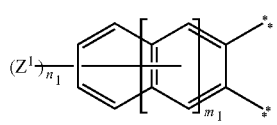

(1)-21

In Formula (1)-21, $m_1$ is an integer of from 0 to 2; $n_1$ is an integer of from 0 to 2 $m_1$+4; $Z^1$ is an alkoxy group, an aryloxy group, a dialkylamino group, a diarylamino group, an alkylarylamino group, an alkylthio group, or an arylthio group, and in a case in which $n_1$ is an integer of 2 or more, such a plurality of $Z^1$'s may be the same as or different from each other; and one bond marked with a symbol ** is formed toward a carbon atom of a formyl group, as one subject to which G is bound, and other bond marked therewith is formed toward a carbon atom of a carbonyl group, as other subject to which G is bound.

In Formula (1)-21, $m_1$ is an integer of from 0 to 2 (0, 1, or 2), and defines the number of ring skeleton(s) included in the aromatic hydrocarbon group. In other words, the aromatic hydrocarbon group in a case in which $m_1$ is 0 is a 1,2-phenylene group, the aromatic hydrocarbon group in a case in which $m_1$ is 1 is a naphthalene-2,3-diyl group, and the aromatic hydrocarbon group in a case in which $m_1$ is 2 is an anthracene-2,3-diyl group.

In Formula (1)-21, $n_1$ is an integer of from 0 to 2 $m_1$+4, and represents the number of bond(s) to the aromatic hydrocarbon group of $Z^1$.

In other words, in a case in which $m_1$ is 0, $n_1$ is an integer of from 0 to 4, preferably an integer of from 0 to 3, more preferably an integer of from 0 to 2, and still more preferably 0 or 1.

In a case in which $m_1$ is 1, $n_1$ is an integer of from 0 to 6, preferably an integer of from 0 to 4, more preferably an integer of from 0 to 3, still more preferably an integer of from 0 to 2, and particularly preferably 0 or 1.

In a case in which $m_1$ is 2, $n_1$ is an integer of from 0 to 8, preferably an integer of from 0 to 4, more preferably an integer of from 0 to 3, still more preferably an integer of from 0 to 2, and particularly preferably 0 or 1.

In Formula (1)-21, $Z^1$ is an alkoxy group, an aryloxy group, a dialkylamino group, a diarylamino group, an alkylarylamino group, an alkylthio group, or an arylthio group, and is the same as in the substituent included in the aromatic hydrocarbon group or aromatic heterocyclic group in G.

In a case in which $n_1$ is an integer of 2 or more and a plurality of $Z^1$'s are present (the compound (1) has a plurality of $Z^1$'s), such a plurality of $Z^1$'s may be the same as or different from each other. In other words, such $Z^1$'s may be here all the same, may be all different, or may be only partially the same.

In a case in which $n_1$ is an integer other than 0, the position of $Z^1$ bound to the aromatic hydrocarbon group is not particularly limited.

In Formula (1)-21, one bond marked with a symbol  is formed toward a carbon atom as one subject to which G is bound, namely, a carbon atom in a carbonyl group, to which a hydrogen atom is bound, in Formula (1). Further, other bond marked with a symbol  is formed toward a carbon atom as other subject to which G is bound, namely, a carbon atom in a carbonyl group, to which X is bound, in Formula (1).

In Formula (1), X is a group represented by Formula (1)-11, (1)-12, (1)-13, (1)-14, or (1)-15. A bond marked with a symbol * is formed toward a carbon atom to which X is bound, namely, a carbon atom in a carbonyl group, to which G is bound, in Formula (1).

In Formula (1)-11, (1)-12, (1)-13 or (1)-14, $R^{11}$, $R^{12}$, $R^{13}$, $R^{22}$, $R^{23}$, $R^{24}$, $R^{32}$, $R^{33}$, $R^{41}$, $R^{42}$, $R^{43}$, and $R^{44}$ are each independently a hydrogen atom or a hydrocarbon group.

In Formula (1)-12, (1)-13 or (1)-15, $R^{21}$, $R^{31}$, $R^{51}$, and $R^{52}$ are each independently a hydrocarbon group.

In other words, $R^{11}$, $R^{12}$ and $R^{13}$ (hereinafter, sometimes abbreviated as "$R^{11}$ to $R^{13}$") in Formula (1)-11 may be all the same, may be all different, or may be only partially the same.

Similarly, $R^{21}$, $R^{22}$, $R^{23}$ and $R^{24}$ (hereinafter, sometimes abbreviated as "$R^{21}$ to $R^{24}$") in Formula (1)-12 may be all the same, may be all different, or may be only partially the same.

Similarly, $R^{31}$, $R^{32}$, and $R^{33}$ (hereinafter, sometimes abbreviated as "$R^{31}$ to $R^{33}$") in Formula (1)-13 may be all the same, may be all different, or may be only partially the same.

Similarly, $R^{41}$, $R^{42}$, $R^{43}$ and $R^{44}$ (hereinafter, sometimes abbreviated as "$R^{41}$ to $R^{44}$") in Formula (1)-14 may be all the same, may be all different, or may be only partially the same.

Similarly, $R^{51}$ and $R^{52}$ (hereinafter, sometimes abbreviated as "$R^{51}$ to $R^{52}$") in Formula (1)-15 may be the same as or different from each other.

Each of the hydrocarbon groups in $R^{11}$ to $R^{13}$, $R^{21}$ to $R^{24}$, $R^{31}$ to $R^{33}$, $R^{41}$ to $R^{44}$, and $R^{51}$ to $R^{52}$ (hereinafter, sometimes abbreviated as "for example, $R^{11}$ to $R^{13}$") is a monovalent hydrocarbon group, and may be any of an aliphatic hydrocarbon group or an aromatic hydrocarbon group (aryl group), or may be an aliphatic hydrocarbon group in which one or more hydrogen atoms are/is substituted with aromatic hydrocarbon group(s) or may be a polycyclic hydrocarbon group obtained by ring-fusion of a cyclic aliphatic hydrocarbon group and an aromatic hydrocarbon group.

The aliphatic hydrocarbon group in, for example, $R^{11}$ to $R^{13}$ may be any of a saturated aliphatic hydrocarbon group (alkyl group) or an unsaturated aliphatic hydrocarbon group.

The alkyl group in, for example, $R^{11}$ to $R^{13}$ may be any of a linear, branched, or cyclic alkyl group, and may be any of a monocyclic or polycyclic alkyl group, in a case in which the alkyl group is a cyclic alkyl group. The alkyl group preferably has from 1 to 20 carbon atoms.

The linear or branched alkyl group preferably has from 1 to 20 carbon atoms, and examples of the linear or branched alkyl group include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a 1-methylbutyl group, a n-hexyl group, a 2-methylpentyl group, a 3-methylpentyl group, a 2,2-dimethylbutyl group, a 2,3-dimethylbutyl group, a n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, a n-octyl group, an isooctyl group, a 2-ethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group.

The cyclic alkyl group preferably has from 3 to 20 carbon atoms, and examples of the cyclic alkyl group include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group, and further include such a cyclic alkyl group in which one or more hydrogen atoms are/is substituted with a linear, branched, or cyclic alkyl group. Examples of the linear, branched, or cyclic alkyl group with which hydrogen atom(s) are/is substituted include the above exemplified as alkyl groups in, for example, $R^{11}$ to $R^{13}$.

The unsaturated aliphatic hydrocarbon group in, for example, $R^{11}$ to $R^{13}$ may be any of a linear, branched, or cyclic unsaturated aliphatic hydrocarbon group, and may be any of a monocyclic or polycyclic unsaturated aliphatic hydrocarbon group in a case in which the unsaturated aliphatic hydrocarbon group is a cyclic unsaturated aliphatic hydrocarbon group. The unsaturated aliphatic hydrocarbon group preferably has from 2 to 20 carbon atoms.

Examples of the unsaturated aliphatic hydrocarbon group in, for example, $R^{11}$ to $R^{13}$ include a group obtained by substituting one or more single bonds (C—C) between carbon atoms in the alkyl group in, for example, $R^{11}$ to $R^{13}$, with double bond(s) (C=C) or triple bond(s) (CC) being unsaturated bond(s).

The number of such unsaturated bond(s) in the unsaturated aliphatic hydrocarbon group may be only one, or two or more, and, in a case where the number is two or more, such unsaturated bonds may correspond to only double bonds or triple bonds, or may correspond to a mixture of a double bond and a triple bond.

The position(s) of the unsaturated bond(s) in the unsaturated aliphatic hydrocarbon group are/is not particularly limited.

Preferable examples of the unsaturated aliphatic hydrocarbon group in, for example, to $R^{13}$ include an alkenyl group and an alkynyl group which are linear or branched, and cycloalkenyl group and a cycloalkynyl group which are cyclic, each corresponding to the above group having one unsaturated bond.

Examples of the alkenyl group include an ethenyl group (vinyl group), a 2-propenyl group (allyl group), and a cyclohexenyl group.

The aryl group in, for example, $R^{11}$ to $R^{13}$ may be any of a monocyclic or polycyclic aryl group, and preferably has from 6 to 20 carbon atoms. Examples of such an aryl group include a phenyl group, a 1-naphthyl group, a 2-naphthyl group, an o-tolyl group, a m-tolyl group, a p-tolyl group, and a xylyl group (dimethylphenyl group), and further include such an aryl group in which one or more hydrogen atoms are/is substituted with such an aryl group or the alkyl group in for example, $R^{11}$ to $R^{13}$. Such an aryl group having a substituent preferably has from 6 to 20 carbon atoms also including carbon atom(s) of the substituent.

Examples of the aliphatic hydrocarbon group in $R^{11}$ to $R^{13}$, in which one or more hydrogen atoms are/is substituted with aromatic hydrocarbon group(s) (aryl group(s)), include an arylalkyl group (aralkyl group) such as a phenylmethyl group (benzyl group) or a 2-phenylethyl group (phenethyl group), in a case in which the number of hydrogen atom(s) substituted is 1.

In Formula (1)-11, in a case in which two or more of $R^{11}$, $R^{12}$, and $R^{13}$ are hydrocarbon groups, the hydrocarbon groups may be bound to each other to form a ring together with carbon atoms (carbon atoms included in the imidazole skeleton) to which the hydrocarbon groups are bound. The "two or more hydrocarbon groups bound to each other" refers to a case in which only two or all (three) of $R^{11}$ to $R^{13}$ are hydrocarbon groups and only any two hydrocarbon groups are bound to each other, and a case in which all (three) of $R^{11}$ to $R^{13}$ are hydrocarbon groups and all the hydrocarbon groups are bound to one another. In both the cases, the hydrocarbon groups are bound with carbon atoms being bound to each other.

In a case in which two or more hydrocarbon groups are bound to each other, the position at which carbon atoms are bound (binding position) is not particularly limited. For example, in a case in which the hydrocarbon groups bound are linear or branched, the binding position may be located on a carbon atom at any end of the hydrocarbon groups, may be located on a carbon atom at any so-called root, directly bound to carbon atoms included in the imidazole skeleton of the hydrocarbon group, or may be located on a carbon atom between the end and the root. In this regard, in a case in which the hydrocarbon groups bound are cyclic, or have both a linear structure and a cyclic structure, the binding position may be located on a carbon atom at the root or on any carbon atom other than such a carbon atom.

In a case in which two hydrocarbon groups of $R^{11}$ to $R^{13}$ are bound to each other, a ring formed may be any of a monocyclic or polycyclic ring. In such a case, the group represented by Formula (1)-11 has a structure in which the imidazole skeleton and a ring formed by binding the hydrocarbon groups to each other are ring-fused.

In Formula (1)-12, in a case in which two or more of $R^{21}$, $R^{22}$, $R^{23}$, and $R^{24}$ are hydrocarbon groups, the hydrocarbon groups may be bound to each other to form a ring together with nitrogen atoms to which the hydrocarbon groups are bound and a carbon atom (the same carbon atom to which all three nitrogen atoms are bound) bound to the nitrogen atoms. The "two or more hydrocarbon groups bound to each other" is meant to be the same as a case in which any hydrocarbon groups of $R^{11}$ to $R^{13}$ are bound to each other, as described above. For example, such binding encompasses a case in which only two, only three, or all (four) of $R^{21}$ to $R^{24}$ are hydrocarbon groups and only any two or three hydrocarbon groups are bound to one another and a case in which all (four) of $R^{21}$ to $R^{24}$ are hydrocarbon groups and all the hydrocarbon groups are bound to one another, and the way of binding of the hydrocarbon groups is also the same as in the case of $R^{11}$ to $R^{13}$.

In Formula (1)-13, in a case in which two or more of $R^{31}$, $R^{32}$, and $R^{33}$ are hydrocarbon groups, the hydrocarbon groups may be bound to each other to form a ring together with nitrogen atoms or a carbon atom, to which the hydrocarbon groups are bound, and carbon atom bound to the nitrogen atoms or nitrogen atoms bound to the carbon atom. The "two or more hydrocarbon groups bound to each other" is meant to be the same as a case in which any hydrocarbon groups of $R^{11}$ to $R^{13}$ are bound to each other, as described above. For example, such binding encompasses a case in which only two or all (three) of $R^{31}$ to $R^{33}$ are hydrocarbon groups and only any two hydrocarbon groups are bound to each other and a case in which all (three) of $R^{31}$ to $R^{33}$ are hydrocarbon groups and all the hydrocarbon groups are bound to one another, and the way of binding of the hydrocarbon groups is also the same as in the case of $R^{11}$ to $R^{13}$.

In Formula (1)-14, in a case in which two or more of $R^{41}$, $R^{42}$, $R^{43}$, and $R^{44}$ are hydrocarbon groups, the hydrocarbon groups may be bound to each other to form a ring together with nitrogen atoms to which the hydrocarbon groups are bound and a carbon atom (the same carbon atom to which all three nitrogen atoms are bound) bound to the nitrogen atoms. The "two or more hydrocarbon groups bound to each other" is meant to be the same as a case in which any hydrocarbon groups of $R^{11}$ to $R^{13}$ are bound to each other, as described above. For example, such binding encompasses a case in which only two, only three, or all (four) of $R^{41}$ to $R^{44}$ are hydrocarbon groups and only any two or three hydrocarbon groups are bound to one another and a case in which all (four) of $R^{41}$ to $R^{44}$ are hydrocarbon groups and all the hydrocarbon groups are bound to one another, and the way of binding of the hydrocarbon groups is also the same as in the case of $R^{11}$ to $R^{13}$.

In Formula (1)-15, $R^{51}$ and $R^{52}$ (hydrocarbon group) may be bound to each other to form a ring together with a nitrogen atom to which the hydrocarbon groups are bound. The way of binding of the hydrocarbon groups here is the same as in the case of $R^{11}$ to $R^{13}$.

The compound (1) is classified to a compound represented by the following Formula (1)-1 (hereinafter, sometimes abbreviated as "compound (1)-1"), a compound represented by the following Formula (1)-2 (hereinafter, sometimes abbreviated as "compound (1)-2"), a compound represented by the following Formula (1)-3 (hereinafter, sometimes abbreviated as "compound (1)-3"), a compound represented by the following Formula (1)-4 (hereinafter, sometimes abbreviated as "compound (1)-4"), and a compound represented by the following Formula (1)-5 (hereinafter, sometimes abbreviated as "compound (1)-5").

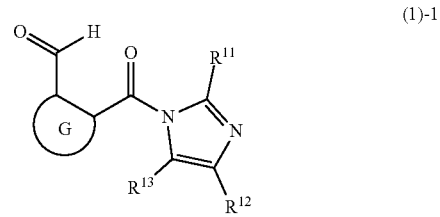

(1)-1

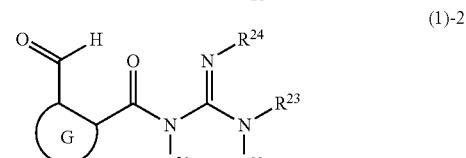

(1)-2

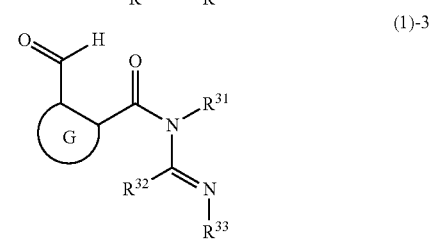

(1)-3

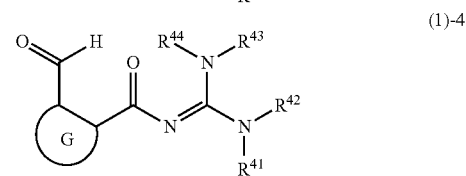

(1)-4

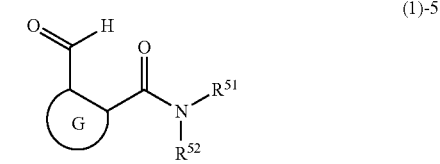

(1)-5

In Formula (1)-1 to Formula (1)-5, $R^{11}$, $R^{12}$, $R^{13}$, $R^{21}$, $R^{22}$, $R^{23}$, $R^{24}$, $R^{31}$, $R^{32}$, $R^{33}$, $R^{41}$, $R^{42}$, $R^{43}$, $R^{44}$, $R^{51}$, and $R^{52}$ have the same meanings as described above.

Preferable examples of the compound (1)-1 include a compound represented by the following Formula (1)-1A (hereinafter, sometimes abbreviated as "compound (1)-1A")

and a compound represented by the following Formula (1)-1B (hereinafter, sometimes abbreviated as "compound (1)-1B").

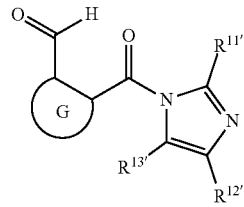
(1)-1A

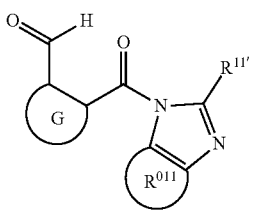
(1)-1B

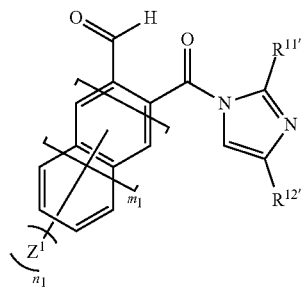
(1)-1A-1

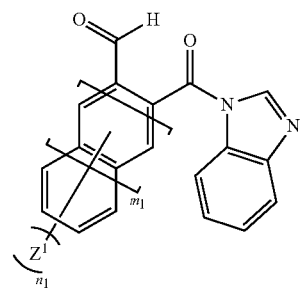
(1)-1B-1

In Formula (1)-1A and Formula (1)-1B, G has the same meaning as described above; $R^{11'}$, and $R^{13'}$ are each independently a hydrogen atom or a hydrocarbon group; and $R^{011}$ is a hydrocarbon ring.

In Formula (1)-1A and Formula (1)-1B, $R^{11'}$, $R^{12'}$, and $R^{13'}$ are each independently a hydrogen atom or a hydrocarbon group.

The hydrocarbon groups in $R^{11'}$, $R^{12'}$, and $R^{13'}$ are the same as the hydrocarbon groups in $R^{11}$ to $R^{13}$ except that no ring is formed by binding to one another. In other words, the compound (1)-1A has no structure obtained by ring-fusion with the imidazole skeleton, described in Formula (1)-1A, even in a case in which $R^{11'}$, $R^{12'}$, and $R^{13'}$ are each any group.

$R^{11'}$, $R^{12'}$, and $R^{13'}$ are each preferably a hydrogen atom, an alkyl group, or an aryl group.

In Formula (1)-1B, $R^{011}$ is a hydrocarbon ring. In other words, $R^{011}$ in Formula (1)-1B is a hydrocarbon ring (cyclic hydrocarbon group) in which two adjacent carbon atoms in the imidazole skeleton are shared with the imidazole skeleton and ring-fused with the imidazole skeleton.

The compound (1)-1B is a compound (1)-1 in which $R^{12}$ and $R^{13}$ being hydrocarbon groups are bound to each other to form a ring.

In Formula (1)-1B, $R^{011}$ may be either monocyclic or polycyclic, and is preferably a saturated aliphatic hydrocarbon ring such as a cyclohexane ring, or an aromatic hydrocarbon ring such as a benzene ring or a naphthalene ring.

Preferable examples of the compound (1)-1A include one in which at least one of $R^{11'}$, $R^{12'}$, or $R^{13'}$ is a hydrogen atom.

Preferable examples of the compound (1)-1B include one in which $R^{011}$ is an aromatic hydrocarbon ring.

More preferable examples of the compound (1)-1 include any compound represented below, and such any compound in which one or more hydrogen atoms bound to any carbon atom included in a nitrogen-containing ring skeleton are/is each substituted with an alkyl group having from 1 to 5 carbon atoms. The "nitrogen-containing ring skeleton" constitutes X in Formula (1).

In Formula (1)-1A-1 and Formula (1)-1B-1, $m_1$, $n_1$, $Z^1$, $R^{11'}$, and $R^{12'}$ have the same meanings as described above.

Preferable examples of the compound (1)-2 include a compound represented by the following Formula (1)-2A (hereinafter, sometimes abbreviated as "compound (1)-2A"), a compound represented by the following Formula (1)-2B (hereinafter, sometimes abbreviated as "compound (1)-2B"), a compound represented by the following Formula (1)-2C (hereinafter, sometimes abbreviated as "compound (1)-2C"), a compound represented by the following Formula (1)-2D (hereinafter, sometimes abbreviated as "compound (1)-2D"), and a compound represented by the following Formula (1)-2E (hereinafter, sometimes abbreviated as "compound (1)-2E").

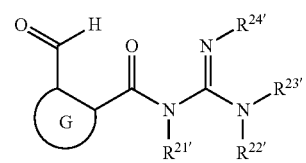
(1)-2A

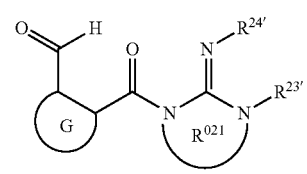
(1)-2B

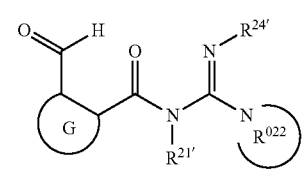
(1)-2C

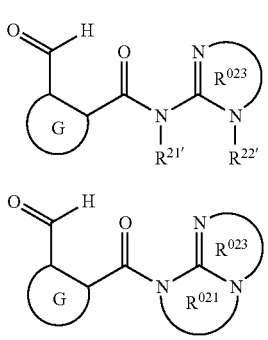

(1)-2D (1)-2E

In Formula (1)-2A to Formula (1)-2E, G has the same meaning as described above; $R^{21'}$ is a hydrocarbon group; $R^{22'}$, $R^{23'}$, and $R^{24'}$ are each independently a hydrogen atom or a hydrocarbon group; $R^{021}$, $R^{022}$, and $R^{023}$ are each independently a nitrogen-containing ring.

In Formula (1)-2A to Formula (1)-2E, $R^{21'}$ is a hydrocarbon group, and $R^{22'}$, $R^{23'}$, and $R^{24'}$ are each independently a hydrogen atom or a hydrocarbon group.

The hydrocarbon groups in $R^{21'}$, $R^{22'}$, $R^{23'}$, and $R^{24'}$ are the same as the hydrocarbon groups in $R^{11}$ to $R^{13}$ except that no ring is formed by binding to one another.

$R^{21'}$ is preferably an alkyl group or an aryl group.

$R^{22'}$, $R^{23'}$, and $R^{24'}$ are each preferably a hydrogen atom, an alkyl group, or an aryl group, and more preferably an alkyl group or an aryl group.

In Formula (1)-2B, $R^{021}$ is a nitrogen-containing ring. The "nitrogen-containing ring" herein means a cyclic structure having a nitrogen atom, besides a carbon atom and a hydrogen atom. In other words, $R^{021}$ in Formula (1)-2B is a ring structure (nitrogen-containing cyclic group) having, as constituent atoms of a ring skeleton, a nitrogen atom bound to a carbon atom of a carbonyl group described in the Formula, a nitrogen atom to which $R^{23'}$ is bound, and one carbon atom located between such two nitrogen atoms. $R^{021}$ may be either monocyclic or polycyclic, and is usually an aliphatic nitrogen-containing ring.

The compound (1)-2B is a compound (1)-2 in which $R^{21}$ and $R^{22}$ being hydrocarbon groups are bound to each other to form a ring.

In Formula (1)-2C, $R^{022}$ is a nitrogen-containing ring. In other words, $R^{022}$ in Formula (1)-2C is a ring structure (nitrogen-containing cyclic group) having one nitrogen atom to which both $R^{21'}$ and $R^{24'}$ are not bound, among three nitrogen atoms described in the Formula, as a constituent atom of the ring skeleton. $R^{022}$ may be either monocyclic or polycyclic, and may be any of an aliphatic nitrogen-containing ring or an aromatic nitrogen-containing ring.

The compound (1)-2C is a compound (1)-2 in which $R^{22}$ and $R^{23}$ being hydrocarbon groups are bound to each other to form a ring.

In Formula (1)-2D, $R^{023}$ is a nitrogen-containing ring. In other words, $R^{023}$ in Formula (1)-2D is a ring structure (nitrogen-containing cyclic group) having, as constituent atoms of a ring skeleton, two nitrogen atoms to which no $R^{21'}$ is bound, among three nitrogen atoms described in the Formula, and one carbon atom between such two nitrogen atoms. $R^{023}$ may be either monocyclic or polycyclic, and may be any of an aliphatic nitrogen-containing ring or an aromatic nitrogen-containing ring.

The compound (1)-2D is a compound (1)-2 in which $R^{23}$ and $R^{24}$ being hydrocarbon groups are bound to each other to form a ring.

In Formula (1)-2E, $R^{021}$ and $R^{023}$ are each a nitrogen-containing ring, $R^{021}$ has the same meaning as in $R^{021}$ in Formula (1)-2B, and $R^{023}$ has the same meaning as $R^{023}$ in Formula (1)-2D.

The compound (1)-2E is a compound (1)-2 in which $R^{21}$ and $R^{22}$ being hydrocarbon groups are bound to each other to form a ring and $R^{23}$ and $R^{24}$ being hydrocarbon groups are bound to each other to form a ring.

Preferable examples of the compound (1)-2A include one in which all $R^{21'}$, $R^{22'}$, $R^{23'}$, and $R^{24'}$ are each an alkyl group or an aryl group.

Preferable examples of the compound (1)-2B include one in which $R^{021}$ is an aliphatic nitrogen-containing ring.

Preferable examples of the compound (1)-2C include one in which $R^{022}$ is an aliphatic nitrogen-containing ring.

Preferable examples of the compound (1)-2D include one in which $R^{023}$ is an aliphatic nitrogen-containing ring.

Preferable examples of the compound (1)-2E include one in which any one of or both $R^{021}$ and $R^{023}$ are each an aliphatic nitrogen-containing ring.

More preferable examples of the compound (1)-2 include any compound represented below, and such any compound in which one or more hydrogen atoms bound to any carbon atom included in a nitrogen-containing ring skeleton are/is each substituted with an alkyl group having from 1 to 5 carbon atoms. The "nitrogen-containing ring skeleton" constitutes X in Formula (1).

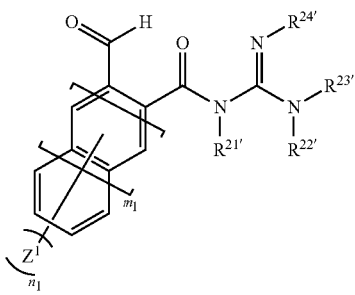

(1)-2A-1

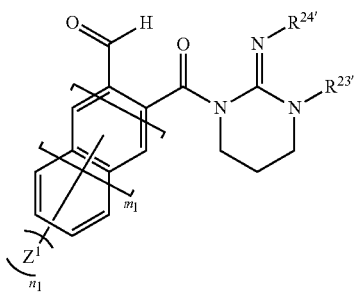

(1)-2B-1

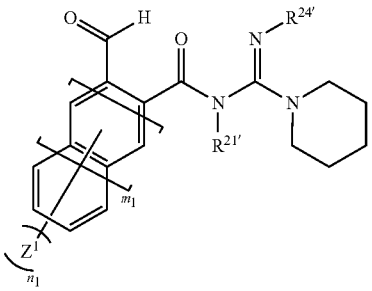

(1)-2C-1

-continued (1)-2D-1

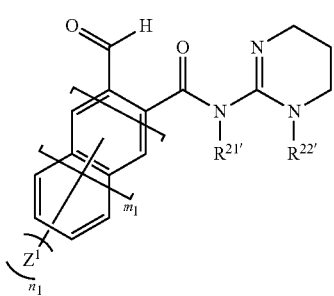

(1)-2E-1

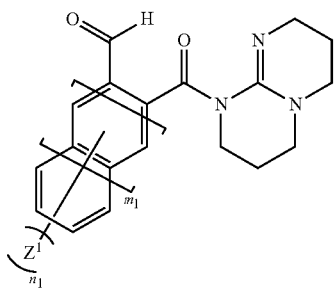

In Formula (1)-2A-1 to Formula (1)-2E-1, $m_1$, $n_1$, $Z^1$, $R^{21'}$, $R^{22'}$, $R^{23'}$, and $R^{24'}$ have the same meanings as described above.

Preferable examples of the compound (1)-3 include a compound represented by the following Formula (1)-3A (hereinafter, sometimes abbreviated as "compound (1)-3A"), a compound represented by the following Formula (1)-3B (hereinafter, sometimes abbreviated as "compound (1)-3B"), a compound represented by the following Formula (1)-3C (hereinafter, sometimes abbreviated as "compound (1)-3C"), and a compound represented by the following Formula (1)-3D (hereinafter, sometimes abbreviated as "compound (1)-3D").

(1)-3A

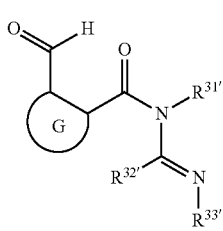

(1)-3B

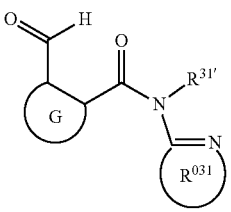

(1)-3C

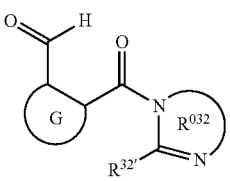

-continued (1)-3D

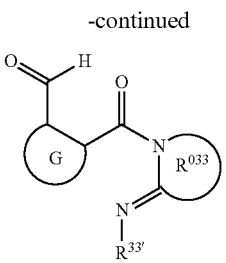

In Formula (1)-3A to Formula (1)-3D, G has the same meaning as described above; $R^{31'}$ is a hydrocarbon group; $R^{32'}$ and $R^{33'}$ are each independently a hydrogen atom or a hydrocarbon group; and $R^{o31}$, $R^{o32}$, and $R^{o33}$ are each independently a nitrogen-containing ring.

In Formula (1)-3A to Formula (1)-3D, $R^{31'}$ is a hydrocarbon group, and $R^{32'}$ and $R^{33'}$ are each independently a hydrogen atom or a hydrocarbon group.

The hydrocarbon groups in $R^{31'}$, $R^{32'}$, and $R^{33'}$ are the same as the hydrocarbon groups in $R^{11}$ to $R^{13}$ except that no ring is formed by binding to one another.

$R^{31'}$ is preferably an alkyl group or an aryl group.

$R^{32'}$ and $R^{33'}$ are each preferably a hydrogen atom, an alkyl group, or an aryl group.

In Formula (1)-3B, $R^{o31}$ is a nitrogen-containing ring. In other words, $R^{o31}$ in Formula (1)-3B is a ring structure (nitrogen-containing cyclic group) having, as constituent atoms of a ring skeleton, one nitrogen atom of two nitrogen atoms described in the Formula, to which no $R^{31'}$ is bound, and one carbon atom located between such two nitrogen atoms. $R^{o31}$ may be either monocyclic or polycyclic, and may be any of an aliphatic nitrogen-containing ring or an aromatic nitrogen-containing ring.

The compound (1)-3B is a compound (1)-3 in which $R^{32}$ and $R^{33}$ being hydrocarbon groups are bound to each other to form a ring.

In Formula (1)-3C, $R^{o32}$ is a nitrogen-containing ring. In other words, $R^{o32}$ in Formula (1)-3C is a ring structure (nitrogen-containing cyclic group) having, as constituent atoms of a ring skeleton, two nitrogen atoms described in the Formula and one carbon atom located between such two nitrogen atoms. $R^{o32}$ may be either monocyclic or polycyclic, and may be any of an aliphatic nitrogen-containing ring or an aromatic nitrogen-containing ring.

The compound (1)-3C is a compound (1)-3 in which $R^{31}$ and $R^{33}$ being hydrocarbon groups are bound to each other to form a ring.

In Formula (1)-3D, $R^{o33}$ is a nitrogen-containing ring. In other words, $R^{o33}$ in Formula (1)-3D is a ring structure (nitrogen-containing cyclic group) having, as constituent atoms of a ring skeleton, one nitrogen atom of two nitrogen atoms described in the Formula, to which no $R^{33'}$ is bound, and one carbon atom located between such two nitrogen atoms. $R^{o33}$ may be either monocyclic or polycyclic, and is usually an aliphatic nitrogen-containing ring.

The compound (1)-3D is a compound (1)-3 in which $R^{31}$ and $R^{32}$ being hydrocarbon groups are bound to each other to form a ring.

Preferable examples of the compound (1)-3A include one in which at least one of $R^{31'}$, $R^{32'}$, or $R^{33'}$ is a hydrogen atom.

Preferable examples of the compound (1)-3B include one in which $R^{o31}$ is an aliphatic nitrogen-containing ring.

Preferable examples of the compound (1)-3C include one in which $R^{o32}$ is an aliphatic nitrogen-containing ring.

Preferable examples of the compound (1)-3D include one in which $R^{033}$ is an aliphatic nitrogen-containing ring.

More preferable examples of the compound (1)-3 include any compound represented below, and such any compound in which one or more hydrogen atoms bound to any carbon atom included in a nitrogen-containing ring skeleton are/is each substituted with an alkyl group having from 1 to 5 carbon atoms. The "nitrogen-containing ring skeleton" constitutes X in Formula (1).

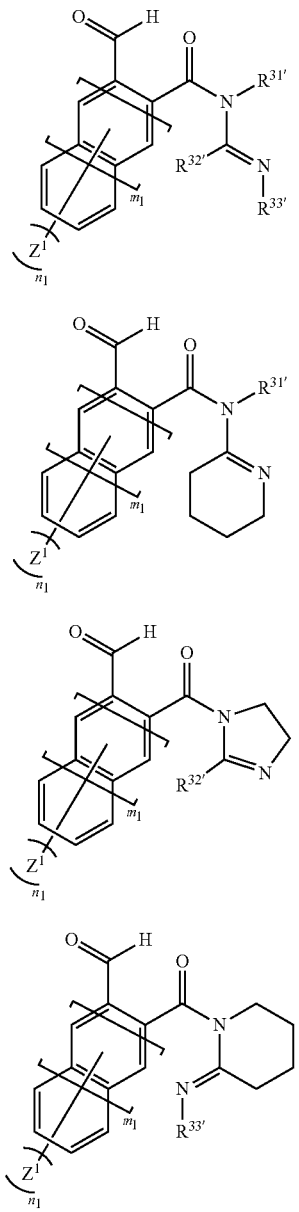

In Formula (1)-3A-1 to Formula (1)-3D-1, $m_1$, $n_1$, $Z^1$, $R^{31\prime}$, $R^{32\prime}$, and $R^{33\prime}$ have the same meanings as described above.

Preferable examples of the compound (1)-4 include a compound represented by the following Formula (1)-4A (hereinafter, sometimes abbreviated as "compound (1)-4A"), a compound represented by the following Formula (1)-4B (hereinafter, sometimes abbreviated as "compound (1)-4B"), a compound represented by the following Formula (1)-4C (hereinafter, sometimes abbreviated as "compound (1)-4C"), a compound represented by the following Formula (1)-4D (hereinafter, sometimes abbreviated as "compound (1)-4D"), and a compound represented by the following Formula (1)-4E (hereinafter, sometimes abbreviated as "compound (1)-4E").

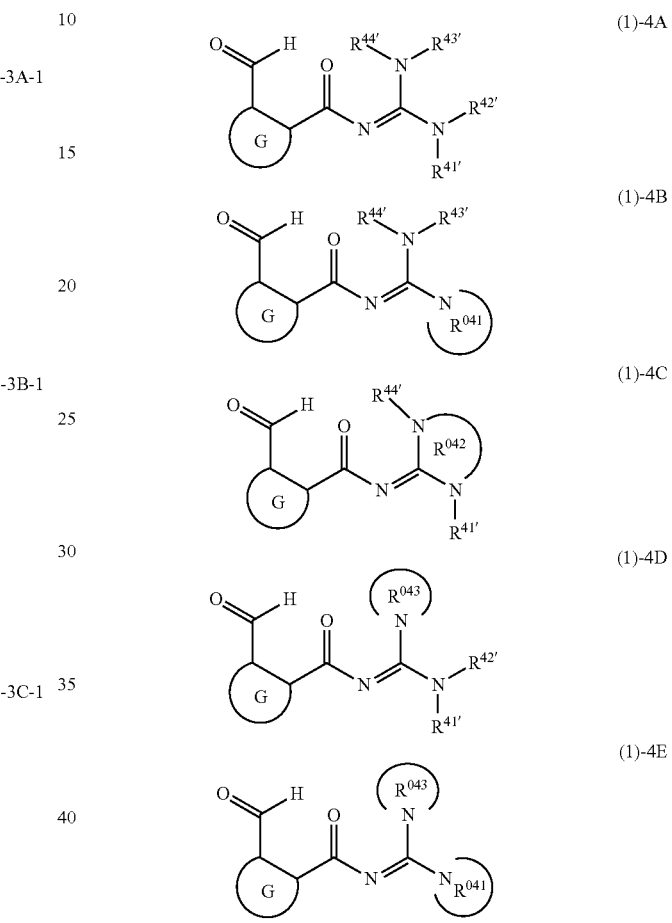

In Formula (1)-4A to Formula (1)-4E, G has the same meaning as described above; $R^{41\prime}$, $R^{42\prime}$, $R^{43\prime}$, and $R^{44\prime}$ are each independently a hydrogen atom or a hydrocarbon group; and $R^{041}$, $R^{042}$, and $R^{043}$ are each independently a nitrogen-containing ring.

In Formula (1)-4A to Formula (1)-4E, $R^{41\prime}$, $R^{42\prime}$, $R^{43\prime}$, and $R^{44\prime}$ are each independently a hydrogen atom or a hydrocarbon group.

The hydrocarbon groups in $R^{41\prime}$, $R^{42\prime}$, $R^{43\prime}$, and $R^{44\prime}$ are the same as the hydrocarbon groups in $R^{11}$ to $R^{13}$ except that no ring is formed by binding to one another.

$R^{41\prime}$, $R^{42\prime}$, $R^{43\prime}$, and $R^{44\prime}$ are each preferably a hydrogen atom, an alkyl group, or an aryl group, and more preferably an alkyl group or an aryl group.

In Formula (1)-4B, $R^{041}$ is a nitrogen-containing ring. In other words, $R^{041}$ in Formula (1)-4B is a ring structure (nitrogen-containing cyclic group) having, as a constituent atom of a ring skeleton, a nitrogen atom corresponding to neither a nitrogen atom bound to a carbon atom of a carbonyl group, nor a nitrogen atom to which both $R^{43\prime}$ and $R^{44\prime}$ are bound, among three nitrogen atoms described in the Formula. $R^{041}$ may be either monocyclic or polycyclic, and may be any of an aliphatic nitrogen-containing ring or an aromatic nitrogen-containing ring.

The compound (1)-4B is a compound (1)-4 in which $R^{41}$ and $R^{42}$ being hydrocarbon groups are bound to each other to form a ring.

In Formula (1)-4C, $R^{042}$ is a nitrogen-containing ring. In other words, $R^{042}$ in Formula (1)-4C is a ring structure (nitrogen-containing cyclic group) having, as constituent atoms of a ring skeleton, two nitrogen atoms other than a nitrogen atom bound to a carbon atom of a carbonyl group among three nitrogen atoms described in the Formula, and one carbon atom located between such two nitrogen atoms. $R^{042}$ may be either monocyclic or polycyclic, and is usually an aliphatic nitrogen-containing ring.

The compound (1)-4C is a compound (1)-4 in which $R^{42}$ and $R^{43}$ being hydrocarbon groups are bound to each other to form a ring.

In Formula (1)-4D, $R^{043}$ is a nitrogen-containing ring. In other words, $R^{043}$ in Formula (1)-4D is a ring structure (nitrogen-containing cyclic group) having, as a constituent atom of a ring skeleton, a nitrogen atom corresponding to neither a nitrogen atom bound to a carbon atom of a carbonyl group, nor a nitrogen atom to which both $R^{41'}$ and $R^{42'}$ are bound, among three nitrogen atoms described in the Formula. $R^{043}$ may be either monocyclic or polycyclic, and may be any of an aliphatic nitrogen-containing ring or an aromatic nitrogen-containing ring.

The compound (1)-4D is a compound (1)-4 in which $R^{43}$ and $R^{44}$ being hydrocarbon groups are bound to each other to form a ring.

In Formula (1)-4E, $R^{041}$ and $R^{043}$ are each a nitrogen-containing ring, $R^{041}$ has the same meaning as $R^{041}$ in Formula (1)-4B, and $R^{043}$ has the same meaning as $R^{043}$ in Formula (1)-4D.

The compound (1)-4E is a compound (1)-4 in which $R^{41}$ and $R^{42}$ being hydrocarbon groups are bound to each other to form a ring and $R^{43}$ and $R^{44}$ being hydrocarbon groups are bound to each other to form a ring.

Preferable examples of the compound (1)-4A include one in which all $R^{41'}$, $R^{42'}$, $R^{43'}$, and $R^{44'}$ are each an alkyl group or an aryl group.

Preferable examples of the compound (1)-4B include one in which $R^{041}$ is an aliphatic nitrogen-containing ring.

Preferable examples of the compound (1)-4C include one in which $R^{042}$ is an aliphatic nitrogen-containing ring.

Preferable examples of the compound (1)-4D include one in which $R^{043}$ is an aliphatic nitrogen-containing ring.

Preferable examples of the compound (1)-4E include one in which any one of or both $R^{041}$ and $R^{043}$ are each an aliphatic nitrogen-containing ring.

More preferable examples of the compound (1)-4 include any compound represented below, and such any compound in which one or more hydrogen atoms bound to any carbon atom included in a nitrogen-containing ring skeleton are/is each substituted with an alkyl group having from 1 to 5 carbon atoms. The "nitrogen-containing ring skeleton" constitutes X in Formula (1).

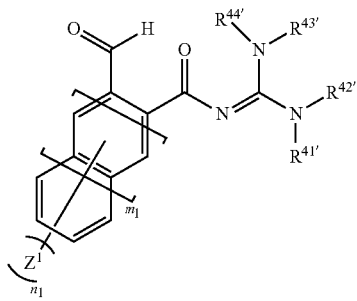

(1)-4A-1

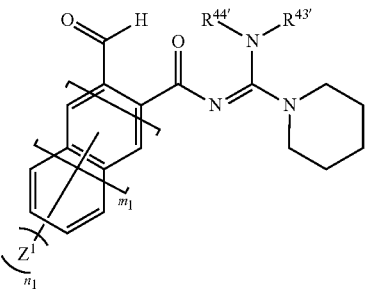

(1)-4B-1

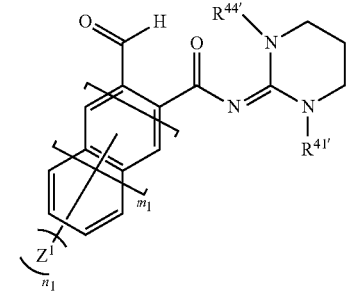

(1)-4C-1

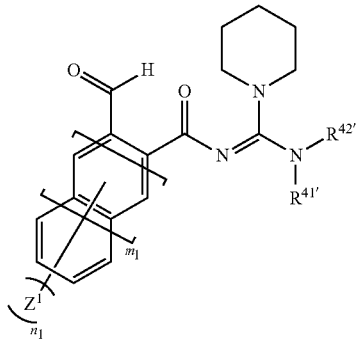

(1)-4D-1

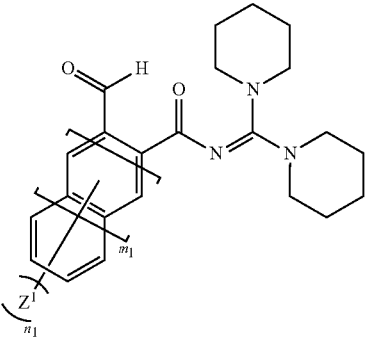

(1)-4E-1

In Formula (1)-4A-1 to Formula (1)-4E-1, $m_1$, $n_1$, $Z^1$, $R^{41'}$, $R^{42'}$, $R^{43'}$ and $R^{44'}$ have the same meanings as described above.

Preferable examples of the compound (1)-5 include a compound represented by the following Formula (1)-5A (hereinafter, sometimes abbreviated as "compound (1)-5A") and a compound represented by the following Formula (1)-5B (hereinafter, sometimes abbreviated as "compound (1)-5B").

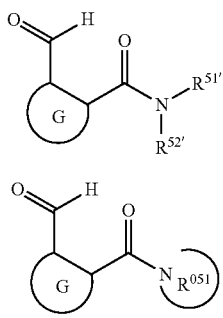

(1)-5A (1)-5B

In Formula (1)-5A and Formula (1)-5B, G has the same meaning as described above; $R^{51'}$ and $R^{52'}$ are each independently a hydrocarbon group; and $R^{051}$ is a nitrogen-containing ring.

In Formula (1)-5A and Formula (1)-5B, $R^{51'}$ and $R^{52'}$ are each independently a hydrocarbon group.

The hydrocarbon groups in $R^{51'}$ and $R^{52'}$ are the same as the hydrocarbon groups in $R^{11}$ to $R^{13}$ except that no ring is formed by binding to each other.

$R^{51'}$ and $R^{52'}$ are each preferably an alkyl group or an aryl group.

In Formula (1)-5B, $R^{051}$ is a nitrogen-containing ring. In other words, $R^{051}$ in Formula (1)-5B is a ring structure (nitrogen-containing cyclic group) having, as a constituent atom of a ring skeleton, a nitrogen atom described in the Formula (nitrogen atom bound to a carbon atom of a carbonyl group). $R^{051}$ may be either monocyclic or polycyclic, and may be any of an aliphatic nitrogen-containing ring or an aromatic nitrogen-containing ring.

The compound (1)-5B is a compound (1)-5 in which $R^{51}$ and $R^{52}$ being hydrocarbon groups are bound to each other to form a ring.

More preferable examples of the compound (1)-5 include any compound represented below, and such any compound in which one or more hydrogen atoms bound to any carbon atom included in a nitrogen-containing ring skeleton are/is each substituted with an alkyl group having from 1 to 5 carbon atoms. The "nitrogen-containing ring skeleton" constitutes X in Formula (1).

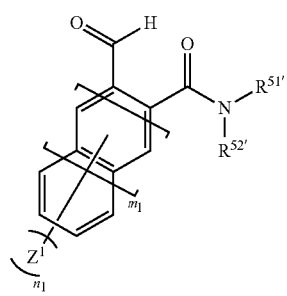

(1)-5A-1

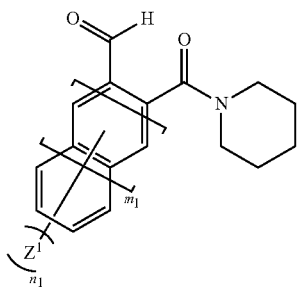

(1)-5B-1

In Formula (1)-5A-1 and Formula (1)-5B-1, $m_1$, $n_1$, $Z^1$, $R^{51'}$, and $R^{52'}$ have the same meanings as described above.

The compound (1)-1, the compound (1)-2, the compound (1)-3, the compound (1)-4, and the compound (1)-5 are merely some examples of the compound (1), and the compound (1) is not limited thereto.

Still more preferable examples of the compound (1) include a compound (1)-1A, a compound (1)-4A, a compound (1)-5A, and a compound (1)-5B.

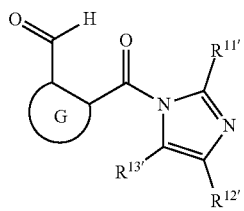

(1)-1A

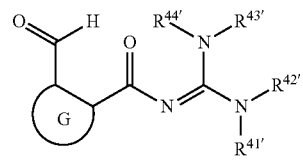

(1)-4A

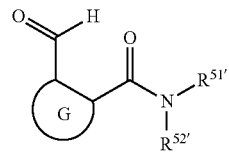

(1)-5A

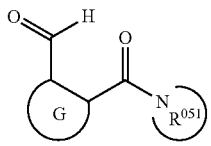

(1)-5B

In Formula (1)-1A, Formula (1)-4A, Formula (1)-5A, and Formula (1)-5B, $R^{12'}$, $R^{13'}$, $R^{41'}$, $R^{42'}$, $R^{43'}$, $R^{44'}$, $R^{51'}$, $R^{52'}$, and $R^{051}$ have the same meanings as described above.

Particularly preferable examples of the compound (1) include a compound (1)-1A-1, a compound (1)-4A-1, a compound (1)-5A-1, and a compound (1)-5B-1.

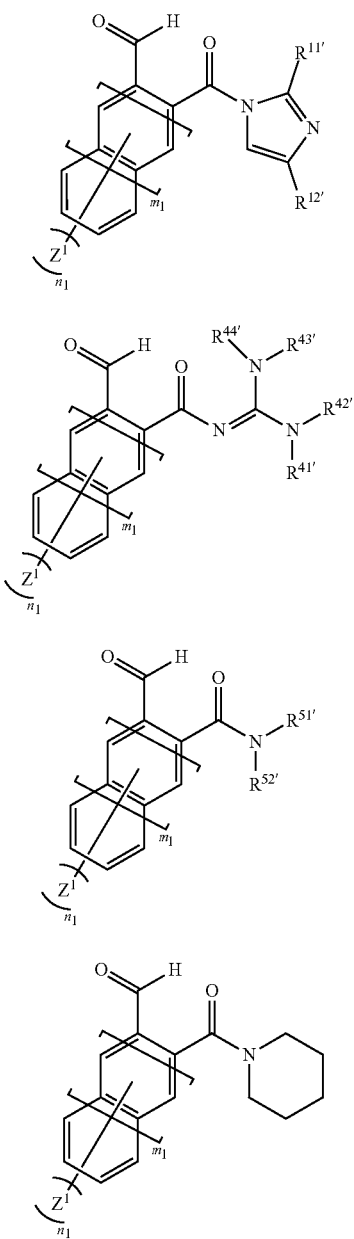

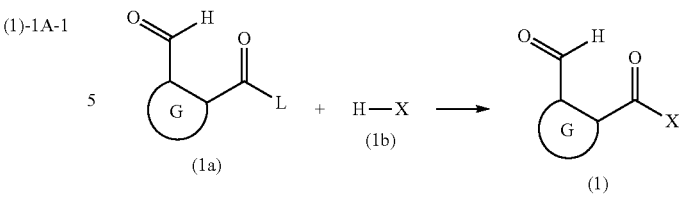

In Formula (1)-1A-1, Formula (1)-4A-1, Formula (1)-5A-1, and Formula (1)-5B-1, $m_1$, $n_1$, $Z^1$, $R^{11\prime}$, $R^{12\prime}$, $R^{41\prime}$, $R^{42\prime}$, $R^{43\prime}$, $R^{44\prime}$, $R^{51\prime}$, and $R^{52\prime}$ have the same meanings as described above.

<Method of Producing Compound (1)>

The compound (1) can be produced using, for example, a procedure for formation of an amide bond.

Examples of such a method of producing the compound (1) include a production method including a step of reacting a compound represented by the following Formula (1a) (hereinafter, sometimes abbreviated as "compound (1a)") and a compound represented by the following Formula (1b) (hereinafter, sometimes abbreviated as "compound (1b)"), thereby obtaining the compound (1) (hereinafter, sometimes abbreviated as "step of producing the compound (1)").

In Formula (1a) and Formula (1b), G and X have the same meanings as described above; and L is a halogen atom.

In Formula (1a), G is the same as G in Formula (1).

In Formula (1a), L is a halogen atom, preferably a chlorine atom or a bromine atom, and more preferably a chlorine atom.

In Formula (1b), X is the same as X in Formula (1).

The compound (1a) and the compound (1b) are reacted in the step of producing the compound (1).

The amount of the compound (1b) used in the reaction is preferably an amount of from 1 time by mol to 5 times by mol, and more preferably an amount of from 1 time by mol to 3.5 times by mol with respect to the amount of the compound (1a) used.

The reaction of the compound (1a) and the compound (1b) is preferably performed using a solvent.

The solvent is not particularly limited, and may be appropriately selected depending on the types of the compound (1a) and the compound (1b). Preferable examples of the solvent include ether such as tetrahydrofuran (THF); halogenated hydrocarbon such as dichloromethane; and amide such as N,N-dimethylformamide or N,N-dimethylacetamide.

The solvent used may be, for example, in a state in which the solvent is mixed with any components other than the solvent, for example, the compound (1a) and the compound (1b) and the components are dissolved or dispersed in advance, or in a state in which the solvent is mixed with such components without dissolution or dispersion of such components other than the solvent in advance.

The solvent may be used singly, or in combination of two or more kinds thereof, and, in a case in which two or more kinds are used in combination, the combination and the ratio can be arbitrarily selected.

The amount of the solvent used in the reaction is not particularly limited, and is, for example, preferably from 1 time by mass to 100 times by mass, and more preferably from 1.5 times by mass to 60 times by mass with respect to the total amount of the compound (1a) and the compound (1b) used.

The temperature in the reaction of the compound (1a) and the compound (1b) may be appropriately modulated in consideration of other reaction conditions, is not particularly limited, and is preferably from −5° C. to 10° C., and more preferably from −2° C. to 5° C.

The reaction time of the compound (1a) and the compound (1b) may be appropriately modulated in consideration of other reaction conditions, is not particularly limited, and is preferably from 0.5 hours to 48 hours, and more preferably from 1 hour to 36 hours.

The reaction of the compound (1a) and the compound (1b) is preferably performed with the amount of moisture in the reaction system being reduced, and the reaction is preferably performed, for example, with a dry solvent or in an atmosphere of an inert gas such as a nitrogen gas, an argon gas, or a helium gas.

The compound (1a) here used may be any commercially available product or any compound obtained by production according to a known method.

A compound (1a) in which L is a chlorine atom is obtained by, for example, reacting a compound in which L in Formula (1a) is substituted with a hydroxyl group (—OH) (namely, a compound represented by Formula "G(—CHO)—C (=O)—OH (wherein G has the same meaning as described above)"), with any chlorinating agent such as thionyl chloride ($SOCl_2$), sulfuryl chloride ($SO_2Cl_2$), phosphoryl chloride ($POCl_3$), oxalyl chloride ($(COCl)_2$), phosphorus trichloride ($PCl_3$), or phosphorus pentachloride ($PCl_5$).

The compound (1) may be taken out in the step of producing the compound (1) by, if necessary, performing a post-treatment according to a known procedure, after completion of the reaction. In other words, the compound (1) may be taken out by condensation, crystallization, reprecipitation, column chromatography, or the like by, if necessary, appropriately using any post-treatment operation such as filtration, washing, extraction, pH adjustment, dewatering, or condensation singly or in combination of two or more kinds. The compound (1) taken out may be, if necessary, further purified by performing any operation such as crystallization, reprecipitation, column chromatography, extraction, or stirring and washing of a crystal with a solvent, singly or in combination of two or more kinds.

The compound (1) may be used in the intended application, without being taken out after completion of the reaction in the step of producing the compound (1).

In a case in which the compound (1a) here used is not any commercially available product, but a compound obtained by production as described above, the compound (1a) may be produced in the reaction and then, if necessary, subjected to the same post-treatment as in the compound (1) and the compound (1a) taken out may be used in the next step, or the compound (1a) may be produced in the reaction and then, if necessary, subjected to a post-treatment and a reaction liquid including the compound (1a) may be used in the next step without taking out of the compound (1a).

While the case in which the compound (1b) and the compound (1a) are reacted is here described, the compound (1) may be obtained by, for example, introducing a protective group into the corresponding group of one that causes a non-objective reaction to easily progress in the reaction with the compound (1a), for example, a compound (1b) having a group represented by Formula "—NH—", then performing the reaction with the compound (1a), and performing deprotection after the reaction. The compound (1) can also be thus easily produced by partially adding or modifying the step in the production method.

While the case in which the compound (1b) and the compound (1a) are reacted is here described, a compound represented by the following Formula (1c) (hereinafter, sometimes abbreviated as "compound (1c)") may be reacted instead of the compound (1a), depending on the type of an objective substance. In such a case, the compound (1) can be produced by the same method as the production method except that the compound (1c) is used instead of the compound (1a).

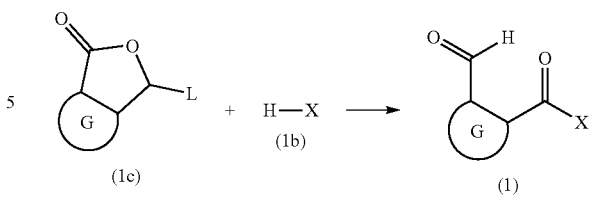

In Formula (1b) and Formula (1c), X, and L have the same meanings as described above.

While the production method including the step of producing the compound (1) is here described as the method of producing the compound (1), the compound (1) may be produced using a combination of raw material compounds other than the compound (1a) and the compound (1b). For example, the compound (1) is also obtained by using a compound represented by Formula "G(—CHO)—C (=O)—OH (wherein G has the same meaning as described above.)") instead of the compound (1a), using a compound represented by Formula "X—C(=O)—X (wherein each X has the same meaning as described above and two X's may be the same as or different from each other.)" instead of the compound (1b), and reacting these compounds.

While the production method including the step of producing the compound (1) is here described as the method of producing the compound (1), the compound (1) may be produced by not a procedure for formation of an amide bond, but formation of a different bond, by use of a combination of raw material compounds other than the compound (1a) and the compound (1b).

The structure of the compound (1) can be confirmed by a known procedure such as nuclear magnetic resonance (NMR) spectroscopy, mass spectrometry (MS), or infrared spectroscopy (IR).

The photobase generator included in the photoreactive composition in the disclosure may be adopted singly, or in combination of two or more kinds thereof, and in a case of two or more kinds, the combination and the ratio can be arbitrarily set.

The content rate of the photobase generator in the photoreactive composition in the disclosure is preferably from 4% by mass to 39% by mass, more preferably from 6% by mass to 36% by mass, and still more preferably from 8% by mass to 33% by mass with respect to the content rate of the base-reactive compound. A content rate of the photobase generator, of 4% by mass or more, allows the reaction of the base-reactive compound to more easily progress. A content rate of the photobase generator, of 39% by mass or less, allows excess use of the photobase generator to be suppressed.

(Specified Polycyclic Aromatic Compound)

The photoreactive composition in the disclosure includes at least one compound (specified polycyclic aromatic compound) selected from the group consisting of a polycyclic aromatic compound having a fused ring structure having two or more rings, as a first polycyclic aromatic compound, and a polycyclic aromatic compound having three or more aromatic rings and having a conjugated structure having any two or more of the three or more aromatic rings, as a second polycyclic aromatic compound.

The specified polycyclic aromatic compound suitably acts as a sensitizer of the photobase generator in the photoreactive composition in the disclosure.

The first polycyclic aromatic compound and the second polycyclic aromatic compound that can be included in the photoreactive composition may be each independently adopted singly, or in combination of two or more kinds thereof, and in a case of two or more kinds, the combination and the ratio can be arbitrarily set. In a case in which the photoreactive composition includes both the first polycyclic aromatic compound and the second polycyclic aromatic compound, the combination and the ratio can be arbitrarily set.

<First Polycyclic Aromatic Compound>

The photoreactive composition in the disclosure may include a polycyclic aromatic compound having a fused ring structure having two or more rings. The first polycyclic aromatic compound is not particularly limited as long as the compound has a fused ring structure having two or more rings.

The first polycyclic aromatic compound preferably has a planar structure as a fused ring structure having two or more rings. The "planar structure" means that such a fused ring structure included in the first polycyclic aromatic compound, preferably, an aromatic ring structure, is fully located on the same plane. In a case in which the first polycyclic aromatic compound has a plurality of fused ring structures each having two or more rings, such at least one fused ring structure preferably has a planar structure, and such a plurality of fused ring structures each having two or more rings are optionally not located on the same plane.

The fused ring structure in the first polycyclic aromatic compound may have one or more of hetero atoms such as an oxygen atom, a sulfur atom, and a nitrogen atom in the structure. Any hydrogen atom in the fused ring structure may be substituted with a substituent. Examples of the substituent include the substituent in the aromatic hydrocarbon group or aromatic heterocyclic group in G of Formula (1).

The first polycyclic aromatic compound may have a fused ring structure having from three rings to five rings, or may have a fused ring structure having three rings or four rings. The first polycyclic aromatic compound may have an aromatic ring having from three rings to five rings, or may have an aromatic ring having three rings or four rings.

Examples of the first polycyclic aromatic compound include naphthoquinone, anthraquinone, xanthene, thioxanthene, xanthone, thioxanthone, anthracene, phenanthrene, phenanthroline, pyrene, pentacene, and any derivative thereof. In particular, anthraquinone, thioxanthone, anthracene, or any derivative thereof is preferable, and thioxanthone, anthracene, or any derivative thereof is more preferable.

The first polycyclic aromatic compound is preferably at least one selected from the group consisting of a compound represented by the following Formula (A), a compound represented by Formula (B), and a compound represented by Formula (C).

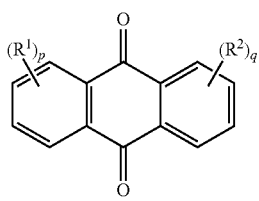

(A)

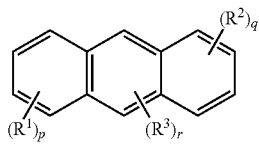

(B)

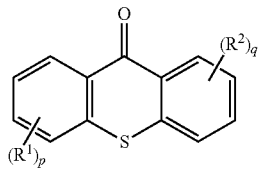

(C)

In Formula (A) to Formula (C), $R^1$, $R^2$, and $R^3$ are each independently an alkyl group, an alkoxy group, an amino group, an alkylthio group, a cyano group, a halogen atom, a nitro group, a haloalkyl group, a hydroxyl group, or a mercapto group, p and q are each independently an integer of from 0 to 4, and r is an integer of from 0 to 2.

In Formula (A), $R^1$ and $R^2$ are each independently preferably a halogen atom or an alkyl group, more preferably a halogen atom, and still more preferably a chlorine atom.

In Formula (A), p and q are each independently preferably an integer of from 0 to 2, more preferably 1 or 2.

In Formula (B), $R^1$, $R^2$, and $R^3$ are each independently preferably an alkyl group, more preferably an alkyl group having from 1 to 10 carbon atoms, still more preferably an alkyl group having from 1 to 5 carbon atoms, particularly preferably an alkyl group having from 3 to 5 carbon atoms, and extremely preferably a branched alkyl group having from 3 to 5 carbon atoms, such as a t-butyl group.

In Formula (B), p and q are each independently preferably an integer of from 0 to 2, and more preferably 0 or 1, and r is preferably 0 or 1, and more preferably 0.

In Formula (C), $R^1$ and $R^2$ are each independently preferably a halogen atom or an alkyl group.

In Formula (C), p and q are each independently preferably an integer of from 0 to 2, and more preferably 0 or 1.

<Second Polycyclic Aromatic Compound>

The photoreactive composition in the disclosure may include a polycyclic aromatic compound having three or more aromatic rings and having a conjugated structure having any two or more of the three or more aromatic rings (provided that the first polycyclic aromatic compound is excluded). The second polycyclic aromatic compound is not particularly limited as long as the compound has three or more aromatic rings and has a conjugated structure having any two or more of the three or more aromatic rings.

The three or more aromatic rings in the second polycyclic aromatic compound may each independently have one or more of hetero atoms such as an oxygen atom, a sulfur atom, and a nitrogen atom in the structure. Any hydrogen atom in the fused ring structure may be substituted with a substituent. Examples of the substituent include the substituent alkyl group being the substituent in the aromatic hydrocarbon group or aromatic heterocyclic group in G of Formula (1).

The second polycyclic aromatic compound has a conjugated structure having any two or more of the three or more aromatic rings. Thus, for example, photosensitizing action in a long-wavelength ultraviolet region of 300 nm or more is excellent. Examples of the conjugated structure having two or more aromatic rings include a benzophenone skeleton.

It is preferable that the second polycyclic aromatic compound is a benzophenone derivative and the benzophenone derivative is a compound in which at least one carbon atom included in an aromatic ring in a benzophenone skeleton is bound to an aromatic ring directly or via a divalent linking group. Examples of the divalent linking group include an alkyl group, an oxygen atom, and a sulfur atom, and an oxygen atom and a sulfur atom are preferable.

The second polycyclic aromatic compound may have from three to five aromatic rings, or may have three or four aromatic rings.

Examples of the second polycyclic aromatic compound include 4-phenylbenzophenone, 4,4'-diphenylbenzophenone, phenyl-(4-phenylsulfanylphenyl)methanone, and any derivative thereof.

The content rate of the specified polycyclic aromatic compound in the photoreactive composition in the disclosure is preferably from 30% by mol to 200% by mol, and more preferably from 50% by mol to 150% by mol with respect to the photobase generator. A content rate of the specified polycyclic aromatic compound, of 30% by mol or more, allows a base to be easily generated from the photobase generator. A content rate of the specified polycyclic aromatic compound, of 200% by mol or less, allows excess use of the specified polycyclic aromatic compound to be suppressed.

(Other Component)

The photoreactive composition in the disclosure may further include any component other than the base-reactive compound, the photobase generator, and the specified polycyclic aromatic compound.

Such other component is not particularly limited and can be arbitrarily selected for any purpose, as long as the effect of the invention is not impaired.

Such other component included in the photoreactive composition may be adopted singly, or in combination of two or more kinds thereof, and in a case of two or more kinds, the combination and the ratio can be arbitrarily set.

Examples of such other component include a compound having only one group that will have the polarity converted by the action of a base and that exhibit reactivity, in one molecule, a compound having only one group that will react under the action of a base, in one molecule, any sensitizer (herein, sometimes referred to as "other sensitizer") other than the specified polycyclic aromatic compound, and a filler, a pigment, and a solvent.

The "compound having only one group that will have the polarity converted by the action of a base and exhibit reactivity, in one molecule" and the "compound having only one group that will react under the action of a base, in one molecule" may be sometimes inclusively referred to as "other base-reactive compound".

The "base-reactive compound" simply described means herein the base-reactive compound (9-2a) or the base-reactive compound (9-2b) described above, unless particularly noted.

<Other Base-Reactive Compound>

The photoreactive composition in the disclosure may include such other base-reactive compound. Such other base-reactive compound can be included, thereby sometimes allowing characteristics such as viscosity to be modulated.

The compound having only one group that will have the polarity converted by the action of a base and that exhibit reactivity, in one molecule, as such other base-reactive compound, is not particularly limited and can be arbitrarily selected for any purpose as long as the compound has such only one group in one molecule.

Similarly, the compound having only one group that will react under the action of a base, in one molecule, as such other base-reactive compound, is not particularly limited and can be arbitrarily selected for any purpose as long as the compound has such only one group in one molecule.

Such other base-reactive compound may be, for example, any of a monomer, an oligomer, and a polymer, or may be any of a low molecular compound or a high molecular compound.

Such other base-reactive compound included in the photoreactive composition in the disclosure may be adopted singly, or in combination of two or more kinds thereof, and in a case of two or more kinds, the combination and the ratio can be arbitrarily set.

The content of such other base-reactive compound in the photoreactive composition in the disclosure is not particularly limited, and may be appropriately modulated depending on, for example, the contents of the base-reactive compound (9-2a) and the base-reactive compound (9-2b).

<Other Sensitizer>

The photoreactive composition in the disclosure may include other sensitizer.

Such other sensitizer is not particularly limited, and examples thereof include benzophenone.

Such other sensitizer may be adopted singly, or in combination of two or more kinds thereof, and in a case of two or more kinds, the combination and the ratio can be arbitrarily set.

The content of such other sensitizer in the photoreactive composition is not particularly limited, and may be appropriately modulated.

The content rate of other sensitizer with respect to the specified polycyclic aromatic compound (specified sensitizer) is preferably 30% by mass or less, more preferably 10% by mass or less, and still more preferably 0% by mass, namely, the photoreactive composition still more preferably include no other sensitizer.

<Filler>

The photoreactive composition in the disclosure may include a filler. A filler can be included, thereby allowing characteristics, for example, the viscosity of the photoreactive composition itself, and the strength of the photoreactive composition (reaction product described below) after the reaction to be modulated.

The filler may be any known filler and is not particularly limited. For example, the filler may be any of a fibrous, plate-like, or granular filler, and the shape, the size, and the material thereof may be each appropriately selected for any purpose.

The filler included in the photoreactive composition may be adopted singly, or in combination of two or more kinds thereof, and in a case of two or more kinds, the combination and the ratio can be arbitrarily set.

The content of the filler in the photoreactive composition is not particularly limited and may be appropriately modulated for any purpose.

<Pigment>

The photoreactive composition in the disclosure may include a pigment. A pigment can be included, thereby allowing, for example, light permeability to be modulated.

The pigment included in the photoreactive composition may be any known pigment such as a white, blue, red, yellow, or green pigment, and is not particularly limited.

The pigment included in the photoreactive composition may be adopted singly, or in combination of two or more kinds thereof, and in a case of two or more kinds, the combination and the ratio can be arbitrarily set.

The content of the pigment in the photoreactive composition is not particularly limited and may be appropriately modulated for any purpose.

<Solvent>

The photoreactive composition in the disclosure may include a solvent. A solvent can be included, thereby allowing handleability to be enhanced.

The solvent is not particularly limited, and may be appropriately selected in consideration of solubility, stability, and the like of the base-reactive compound and the photobase generator.

The solvent is not particularly limited, and examples thereof include halogenated hydrocarbon such as dichloromethane or chloroform; aromatic hydrocarbon such as toluene, o-xylene, m-xylene, or p-xylene; aliphatic hydrocarbon such as hexane, heptane, or octane; carboxylate ester such as ethyl acetate or butyl acetate; ether such as diethyl ether, tetrahydrofuran (THF), or 1,2-dimethoxyethane (dimethylcellosolve); ketone such as acetone, methyl ethyl ketone (MEK), cyclohexanone, or cyclopentanone; nitrile such as acetonitrile; and amide such as N,N-dimethylformamide (DMF) or N,N-dimethylacetamide.

The solvent included in the photoreactive composition may be adopted singly, or in combination of two or more kinds thereof, and in a case of two or more kinds, the combination and the ratio can be arbitrarily set.

The content of the solvent in the photoreactive composition is preferably from 3 times by mass to 20 times by mass, more preferably from 4 times by mass to 15 times by mass, and still more preferably from 5 times by mass to 10 times by mass with respect to the content of the base-reactive compound. The content of the solvent is in such a range, thereby allowing the photoreactive composition to be more enhanced in handleability.

The photoreactive composition is obtained by blending the base-reactive compound, the photobase generator, the specified polycyclic aromatic compound, and, if necessary, any other component. One obtained after blending of such respective components may be adopted as the photoreactive composition as it is, or may be, if necessary, subsequently subjected to, for example, a known purification operation, thereby obtaining the photoreactive composition.

The blending of such respective components may be performed by adding all the components and then mixing them, performing mixing while sequentially adding some of the components, or performing mixing while sequentially adding all the components.

The mixing method is not particularly limited, and may be appropriately selected from known methods including a method involving mixing under rotation of, for example, a stirring bar or a stirring blade; a method involving mixing by use of, for example, a mixer; and a method involving mixing by addition of ultrasonic wave.

The temperature in the blending is not particularly limited as long as the respective components blended are not degraded, and the temperature can be, for example, from 3° C. to 30° C.

The blending time is also not particularly limited as long as the respective components blended are not degraded, and the time can be, for example, from 30 seconds to 1 hour.

It is noted that these blending conditions are merely examples.

<Reaction Product>

The reaction product in the disclosure is obtained by reacting the photoreactive composition. The method of producing the reaction product in the disclosure is described in the section of the method of producing a reaction product in the disclosure, described below.

The shape of the reaction product in the disclosure is, for example, a membranous or linear shape, and can be arbitrarily selected for any purpose.

<Method of Producing Reaction Product>

The method of producing a reaction product in the disclosure includes a step of irradiating the photoreactive composition with light, thereby generating the base from the photobase generator. The base-reactive compound included in the photoreactive composition exhibits reactivity due to conversion of the polarity of a functional group included in the base-reactive compound, by the action of the base generated, or allows a functional group included in the base-reactive compound that will react under the action of the base generated. Thus, a reaction product is obtained by irradiating the photoreactive composition with light to generate the base, thereby reacting the base-reactive compound included in the photoreactive composition.

The photoreactive composition may be attached to an objective substance according to a known procedure, and then, if necessary, pre-baked (dried), thereby forming a photoreactive composition layer, and the photoreactive composition layer may be irradiated with light.

For example, in a case in which a membranous reaction product is produced, the reaction product may be produced by coating an objective substance with the photoreactive composition by use of any of various coaters such as a spin coater, an air knife coater, a blade coater, a bar coater, a gravure coater, a roll coater, a roll knife coater, a curtain coater, a die coater, a knife coater, a screen coater, a meyer bar coater, and a kiss coater, or a coating unit such as an applicator, or immersing an objective substance in the photoreactive composition, thereby allowing the photoreactive composition to be attached to the objective substance.

For example, in a case in which a membranous or linear reaction product is produced, the reaction product may be produced by allowing the photoreactive composition to be attached to an objective substance by use of a printing procedure such as a screen printing method, a flexographic printing method, an offset printing method, an inkjet printing method, a dispenser printing method, a jet dispenser printing method, a gravure printing method, a gravure offset printing method, or a pad printing method.

The pre-baking may be performed in conditions of, for example, from 50° C. to 120° C. and from 1 minute to 10 minutes, and is not particularly limited.

The wavelength of light with which the photoreactive composition is irradiated is not particularly limited, and may be, for example, any wavelength in the ultraviolet to visible region. The wavelength of light with which the photoreactive composition is irradiated may be 10 nm or more, may be 200 nm or more, or may be 300 nm or more. The wavelength of light with which the photoreactive composition is irradiated may be 600 nm or less, may be 500 nm or less, or may be 400 nm or less. In particular, the production method in the disclosure tends to allow the photobase generator to be excellent in optical sensitivity, even in a case in which the wavelength of light with which the photoreactive composition is irradiated is, for example, 300 nm or more in the long-wavelength ultraviolet region. Thus, for example, the light source can be suitably changed from a mercury lamp (short wavelength ultraviolet light; 254 nm) to, for example, an LED light source, and environmental properties and practicality are excellent.

The illuminance of light with which the photoreactive composition is irradiated is, for example, preferably from 1 mW/cm² to 100 mW/cm², more preferably from 5 mW/cm² to 80 mW/cm², and still more preferably from 10 mW/cm² to 60 mW/cm².

The amount of light with which the photoreactive composition is irradiated is, for example, preferably from 300 mJ/cm² to 50000 mJ/cm², more preferably from 1000 mJ/cm² to 40000 mJ/cm², and still more preferably from 5000 mJ/cm² to 20000 mJ/cm².

It is noted that light irradiation conditions here listed are merely examples and are not limited thereto.

Such a reaction product obtained by irradiating the photoreactive composition with light may be further subjected to post-baking (heating treatment after light irradiation).

The post-baking may be performed in conditions of, for example, from 80° C. to 180° C. and from 20 minutes to 2 hours, and is not particularly limited.

The thickness of the reaction product may be appropriately set for any purpose, and is not particularly limited. The thickness of the reaction product is, for example, preferably from 1 µm to 500 µm and more preferably from 5 µm to 200 µm. A reaction product having such a thickness can be formed by, for example, setting the thickness of the photoreactive composition layer to any thickness equal to or more than the thickness of an objective reaction product.

For example, the ratio of the thickness of the reaction product (thickness of photoreactive composition layer after light irradiation) with respect to the thickness of the photoreactive composition layer (thickness of photoreactive composition layer before light irradiation) ([thickness of photoreactive composition layer after light irradiation]/[thickness of photoreactive composition layer before light irradiation]) can be, for example, from 0.2 to 1.0, and can be any of from 0.3 to 1.0, from 0.4 to 1.0, from 0.5 to 1.0, from 0.6 to 1.0, from 0.7 to 1.0, from 0.8 to 1.0, or from 0.9 to 1.0, by further modulation of reaction conditions.

EXAMPLES

Hereinafter, the invention will be more specifically described with reference to Examples, but the invention is not limited by these Examples.

<Production of Compound (1)-5B-101>

A compound (1)-5B-101 was produced by reacting a compound (1a) and a compound (1b), as described below.

In other words, phthalaldehydic acid (8.04 g, 53.6 mmol) was added to thionyl chloride (32.0 g, 269 mmol), dry DMF (4 mL) was further added thereto, and the resultant was stirred at room temperature for 3 hours, thereby allowing a reaction to be performed. After completion of the reaction, unreacted thionyl chloride was distilled off from a reaction liquid under reduced pressure.

Dry THF (20 mL) was separately added to piperidine (13.0 g, 152 mmol), the reaction liquid from which thionyl chloride was distilled off was added thereto, and the resultant was stirred at 0° C. for 4 hours, thereby allowing a reaction to be performed. After completion of the reaction, a solvent was distilled off.

Next, dichloromethane was added to the resulting reaction liquid, and hydrochloric acid having a concentration of 5% by mass was further added and the resultant was shaken in a separating funnel, thereby washing the reaction liquid. Such washing with hydrochloric acid was performed once more, namely, such washing was performed twice in total.

Next, an aqueous saturated sodium hydrogen carbonate solution was added to the reaction liquid after the washing with hydrochloric acid, and shaken in a separating funnel, thereby washing the reaction liquid. Such washing with an aqueous saturated sodium hydrogen carbonate solution was performed once more, namely, such washing was performed twice in total.

Next, an aqueous saturated sodium chloride solution was added to the reaction liquid after the washing with an aqueous saturated sodium hydrogen carbonate solution, and shaken in a separating funnel, thereby washing the reaction liquid. Such washing with an aqueous saturated sodium chloride solution was performed once more, namely, such washing was performed twice in total.

Next, the reaction liquid after the washing with an aqueous saturated sodium chloride solution was purified by silica gel column chromatography with a mixed solvent of ethyl acetate/n-hexane (1/1, volume ratio) as a mobile phase, and a fraction including the objective substance was collected and condensed, thereby obtaining a compound (1)-5B-101 being the objective substance, as a yellow viscous liquid (amount of recovery 11.4 g, rate of recovery 98%).

The analysis results of ¹H-NMR, ¹³C-NMR, and ESI-MS of the resulting compound (1)-5B-101 are shown in Table 1.

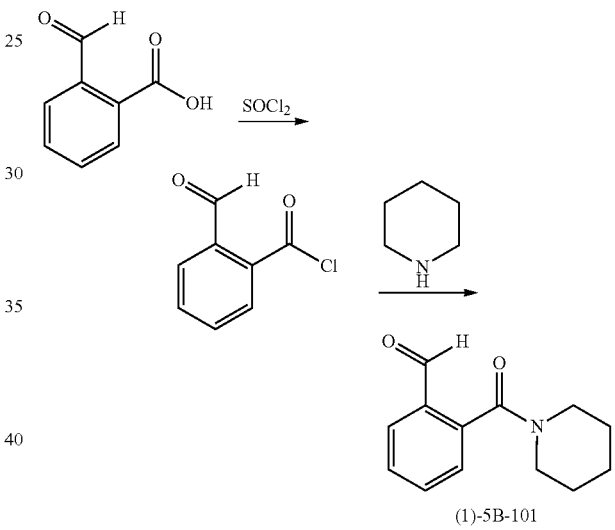

(1)-5B-101

TABLE 1

| ¹H-NMR [δ/ppm] (300 MHz, CDCl₃) | 1.43 (quint, 2H, J = 6.0 Hz, piperidyl-H)<br>1.69 (quint, 3.4H, J = 6.0 Hz, piperidyl-H)<br>3.15 (t, 2H, J = 6.0 Hz. piperidyl-H)<br>3.80 (t, 2H, J = 6.0 Hz. piperidyl-H)<br>7.3-8.0 (m, 4H. Ar—H)<br>10.8 (s, 1H, —CHO) |
|---|---|
| ¹³C-NMR [δ/ppm] (75 MHz, CDCl₃) | 24.3 (sp³ carbon), 25.3 (sp³ carbon)<br>26.0 (sp³ carbon), 42.6 (sp³ carbon)<br>48.0 (sp³ carbon), 126.8 (sp² carbon)<br>129.1 (sp² carbon), 130.0 (sp² carbon)<br>132.5 (sp² carbon), 134.1 (sp² carbon)<br>139.0 (sp² carbon), 167.6 (C—O carbon)<br>190.5 (C=O carbon) |
| ESI-MASS [M + Na]⁺ | Calculated value: 240.10005<br>Measured value: 240.10015 |

The resulting compound (1)-5B-101 was subjected to differential thermal/thermogravimetric (TG-DTA) simultaneous measurement in conditions of a rate of temperature rise of 5° C./min and a measurement temperature range of from 20° C. to 500° C., and it was thus confirmed that the compound was decomposed at 240.2° C.

Test Example 1

Polystyrene (0.060 g, number average molecular weight Mn: 35000), the compound (1)-5B-101 (0.020 g, 33% by mass with respect to polystyrene), 1,8-dichloroanthraquinone (100% by mol with respect to the compound (1)-5B-101) as a specified polycyclic aromatic compound, and chloroform (0.60 g) were blended and stirred at 25° C. for 1 minute, thereby obtaining a testing resin composition.

Next, a silicon plate was coated with the testing resin composition obtained above, according to a spin coating method in conditions of 2000 rpm and 30 seconds, the resulting coating film was heated at 100° C. for 1 minute, and thereafter the coating film was irradiated with light at a wavelength of 365 nm at an illuminance of 50 mW/cm² by use of an LED lamp. The peak intensity (1630 cm⁻¹) derived from the stretching vibration of C=O of an amide group in the compound (1)-5B-101 was here measured with a Fourier transform infrared spectrophotometer (FT-IR) in specified exposure doses (mJ/cm²) illustrated in FIG. 1. The results are illustrated in FIG. 1.

As clear from FIG. 1, as the exposure doses were increased, the peak intensity assigned to a carbonyl group was decreased. The reason is because light irradiation led to generation of a compound (1')-5B-101 as a base from the compound (1)-5B-101 as represented by the following Formula.

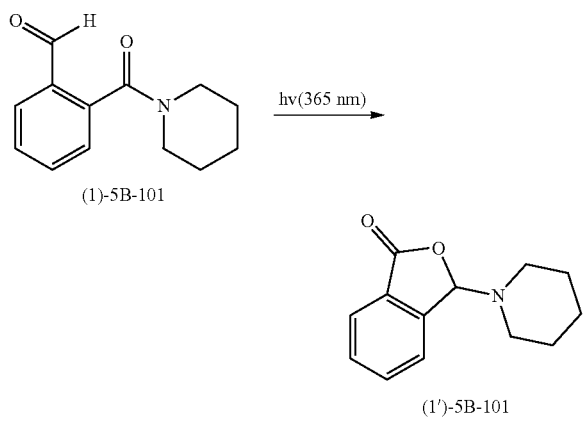

Test Example 2

A testing resin composition was obtained in the same manner as in Test Example 1 except that 2-tert-butylanthracene (tBAnt) was used instead of 1,8-dichloroanthraquinone in Test Example 1.

A coating film was formed in the same manner as in Test Example 1, and the peak intensity derived from the stretching vibration of C=O of an amide group in the compound (1)-5B-101 was measured with a Fourier transform infrared spectrophotometer (FT-IR) in specified exposure doses (mJ/cm²) illustrated in FIG. 1. The results are illustrated in FIG. 1.

As clear from FIG. 1, light irradiation led to generation of a compound (1')-5B-101 as a base from the compound (1)-5B-101, as in Test Example 1.

Test Example 3

A testing resin composition was obtained in the same manner as in Test Example 1 except that thioxanthone (TX) was used instead of 1,8-dichloroanthraquinone in Test Example 1.

A coating film was formed in the same manner as in Test Example 1, and the peak intensity derived from the stretching vibration of C=O of an amide group in the compound (1)-5B-101 was measured with a Fourier transform infrared spectrophotometer (FT-IR) in specified exposure doses (mJ/cm²) illustrated in FIG. 1. The results are illustrated in FIG. 1.

As clear from FIG. 1, light irradiation led to generation of a compound (1')-5B-101 as a base from the compound (1)-5B-101, as in Test Example 1.

Test Example 4

A testing resin composition was obtained in the same manner as in Test Example 1 except that no 1,8-dichloroanthraquinone was used in Test Example 1.

A coating film was formed in the same manner as in Test Example 1, and the peak intensity derived from the stretching vibration of C=O of an amide group in the compound (1)-5B-101 was measured with a Fourier transform infrared spectrophotometer (FT-IR) in specified exposure doses (mJ/cm²) illustrated in FIG. 1. The results are illustrated in FIG. 1.

As clear from FIG. 1, light irradiation led to generation of a compound (1')-5B-101 as a base from the compound (1)-5B-101, as in Test Example 1. However, Test Example 4 exhibited a high peak intensity assigned to a carbonyl group in the same exposure doses, as compared with Test Examples 1 to 3, and thus exhibited a low generating efficiency of the compound (1')-5B-101 as a base from the compound (1)-5B-101, as compared with Test Examples 1 to 3.

Test Example 5

A testing resin composition was obtained in the same manner as in Test Example 1 except that benzophenone was used instead of 1,8-dichloroanthraquinone in Test Example 1.

A coating film was formed in the same manner as in Test Example 1, and the peak intensity derived from the stretching vibration of C=O of an amide group in the compound (1)-5B-101 was measured with a Fourier transform infrared spectrophotometer (FT-IR) in specified exposure doses (mJ/cm²) illustrated in FIG. 1.

However, it was confirmed that Test Example 5 exhibited an peak intensity assigned to a carbonyl group in the same exposure doses, comparable with Test Example 4, and exhibited a low generating efficiency of the compound (1')-5B-101 as a base from the compound (1)-5B-101, as compared with Test Examples 1 to 3.

The results indicated that benzophenone absorbed almost no light at a wavelength of 365 nm and almost no photosensitizing action with light at a wavelength of 365 nm was observed.

<Production of Base-Reactive Compound>

A base-reactive compound (9)-201 was produced as described below.

In other words, dry THF (45 mL) was added to glycidyl methacrylate (6.13 g, 43.1 mmol), and the resulting solution was purged with a nitrogen gas for 30 minutes. Next, the solution after such purging was heated to 70° C., 2,2'-azobis(isobutyronitrile) (AIBN) (0.074 g, 0.45 mmol) was added thereto, and the resultant was heated under flux for 8 hours.

Next, the resulting reaction liquid was cooled to room temperature, THF was added and thereafter ethanol as a poor solvent was added, thereby resulting in precipitation of the objective substance, the resultant was filtered, and the resulting solid was washed with THF, thereby obtaining the objective substance.

The resulting objective substance was subjected repeatedly twice to reprecipitation including dissolving in THF, precipitation by addition of ethanol, taking out by filtration, and washing with THF.

From the foregoing, a base-reactive compound (9)-201 as the objective substance was obtained in the form of a white solid (amount of recovery 4.37 g, rate of recovery 71%).

The analysis results of $^1$H-NMR of the resulting base-reactive compound (9)-201 are shown in Table 2.

The base-reactive compound (9)-201 had a weight average molecular weight (Mw) of 27454 and a molecular weight distribution (Mw/Mn) of 1.52, in terms of standard polystyrene conversion determined according to gel permeation chromatography (GPC).

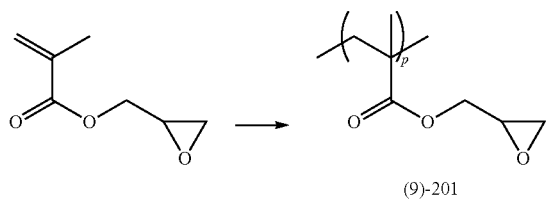

(9)-201

In Formula (9)-201, p is an integer of 2 or more.

TABLE 2

| $^1$H-NMR [δ/ppm] (500 MHz, CDCl$_3$) | 1.0-1.1 (br, 3H, —CH$_3$) |
| --- | --- |
| | 1.9-2.0 (br, 2H, —CH$_2$—C—) |
| | 2.64 (br, 1H, —OCH$_2$—) |
| | 2.85 (br, 1H, —OCH$_2$—) |
| | 3.24 (br, 1H, —CH$_2$CHO—) |
| | 3.82 (br, 1H, —OCOCH$_2$—) |
| | 4.31 (br, 1H, —OCOCH$_2$—) |

Example 1

(Production of Photoreactive Composition)

The base-reactive compound (9)-201 (0.11 g), the compound (1)-5B-101 (0.012 g, 7% by mol with respect to glycidyl methacrylate as a raw material of the base-reactive compound), 2-tert-butylanthracene (tBAnt, 100% by mol with respect to the compound (1)-5B-101) as a specified polycyclic aromatic compound, and chloroform (1.10 g, 10.0 times by mass with respect to the base-reactive compound) were blended, and stirred at 25° C. for 1 minute, thereby obtaining a photoreactive composition.

(Production of Reaction Product)

Figure 2:
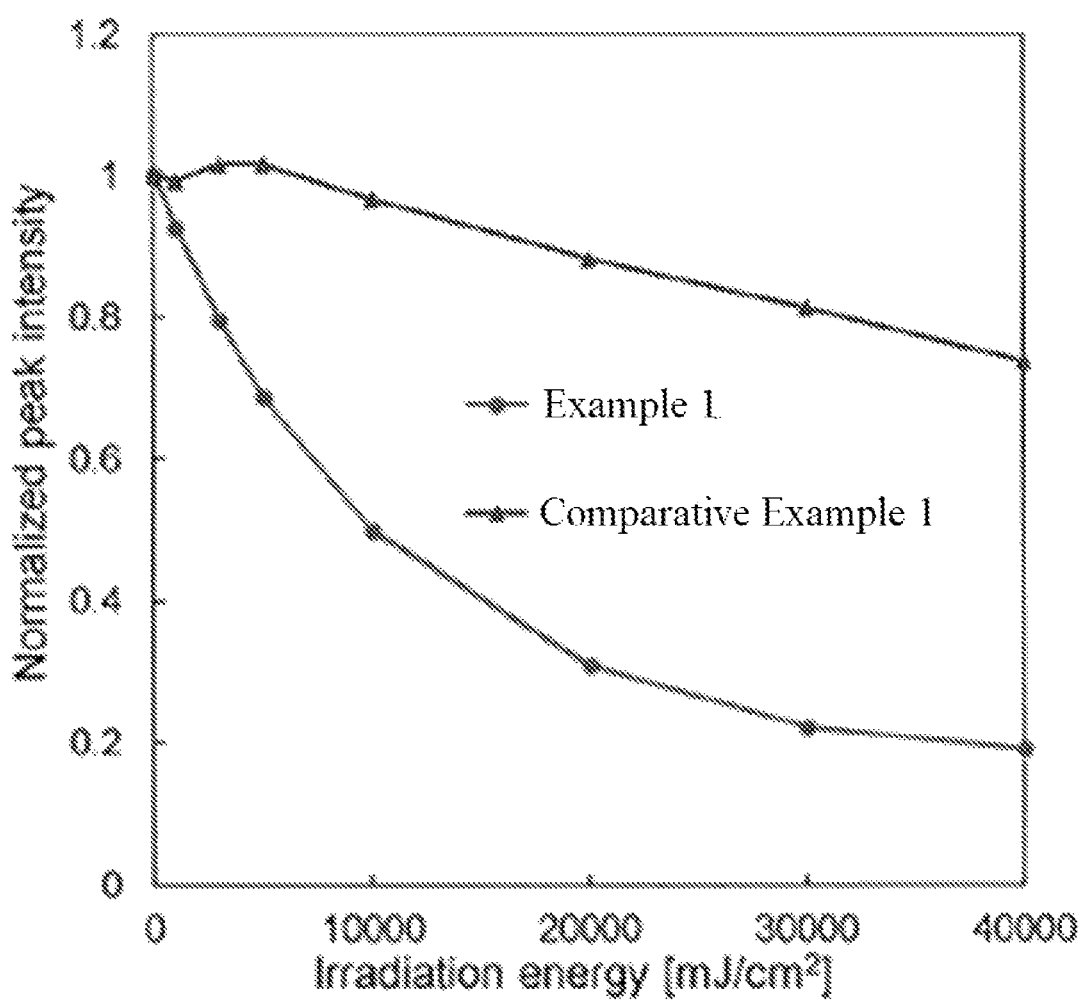
FIG. 2 is a graph illustrating the peak intensity derived from the stretching vibration of C=O of an amide group in a compound (1)-5B-101 in Example 1 and Comparative Example 1.

A silicon wafer was coated with the photoreactive composition obtained above, according to a spin coating method in conditions of 1500 rpm and 30 seconds, and the thickness (the thickness of the coating film before light irradiation) of the resulting coating film was measured. Next, the coating film (photoreactive composition layer) was heated (pre-baked) at 75° C. for 2 minutes, and thereafter the coating film was irradiated with light at a wavelength of 365 nm in each of eight kinds of exposure doses of 0, 1000, 3000, 5000, 10000, 20000, 30000, and 40000 mJ/cm$^2$ at an illuminance of 50 mW/cm$^2$ by use of an LED lamp. The peak intensity (1630 cm$^{-1}$) derived from the stretching vibration of C=O of an amide group in the compound (1)-5B-101 was measured with a Fourier transform infrared spectrophotometer (FT-IR). The results are illustrated in FIG. 2.

Next, each of five coating films irradiated with light in respective exposure doses of 0, 1000, 5000, 20000, and 40000 mJ/cm$^2$ was heated (post-baked) at 100° C. for 90 minutes. Such each coating film, except for that in an exposure dose of 0 mJ/cm$^2$, was tried to be finally formed into a reaction product obtained by polymerization of the base-reactive compound (9)-201.

Figure 3:
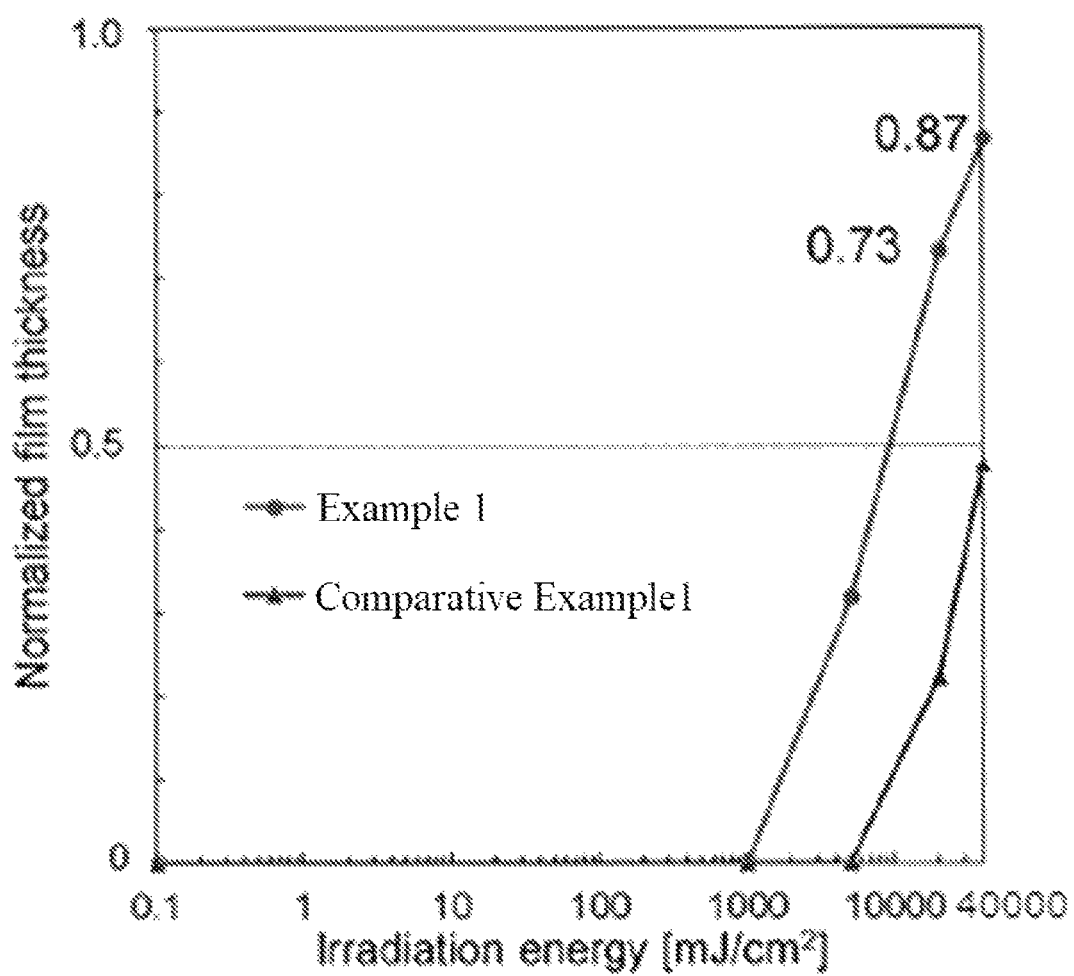
FIG. 3 is a graph illustrating the relationship between the exposure doses and the normalized remaining thickness of a coating film in Example 1 and Comparative Example 1.

Next, such each coating film after post-baking was washed with chloroform, thereafter the thickness of each of such eight coating films washed (thickness of coating film after post-baking) was measured, and the normalized remaining thickness of each of five coating films was calculated according to the following Expression (ii). The results are illustrated in FIG. 3.

[Normalized remaining thickness]=[Thickness of coating film after post-baking]/[Thickness of coating film before light irradiation]     (ii)

Comparative Example 1

A photoreactive composition was obtained in the same manner as in Example 1 except that no 2-tert-butylanthracene was used in Example 1.

A coating film was formed in the same conditions as those in Example 1, and the peak intensity (1630 cm$^{-1}$) derived from the stretching vibration of C=O of an amide group in the compound (1)-5B-101 was measured with a Fourier transform infrared spectrophotometer (FT-IR). The results are illustrated in FIG. 2.

Next, the normalized remaining thickness of the coating film was calculated in the same conditions as those in Example 1. The results are illustrated in FIG. 3.

As clear from FIG. 2, light irradiation led to generation of a compound (1')-5B-101 as a base from the compound (1)-5B-101, in Example 1 and Comparative Example 1. Example 1 exhibited a low peak intensity assigned to a carbonyl group in the same exposure doses, as compared with Comparative Example 1, and thus exhibited a high generating efficiency of the compound (1')-5B-101 as a base from the compound (1)-5B-101, as compared with Comparative Example 1.

As illustrated in FIG. 3, Example 1 exhibited a high normalized remaining thickness in the same exposure doses, as compared with Comparative Example 1. The reason is because Example 1 exhibited a high generating efficiency of the compound (1')-5B-101 as a base from the compound (1)-5B-101, as compared with Comparative Example 1, and thus exhibited high reactivity of the base-reactive compound (9)-201 and a high production efficiency of a reaction product.

It was indicated from the foregoing that Example 1 exhibited excellent optical sensitivity of a photobase generator in the long-wavelength ultraviolet region.

Comparative Example 2

A photoreactive composition was obtained in the same manner as in Example 1 except that Michler's ketone (4,4'-bis(dimethylamino)benzophenone) was used instead of 2-tert-butylanthracene in Example 1.

A silicon wafer was coated with the photoreactive composition in the same conditions as those in Example 1, and furthermore heated, thereby forming a coating film. The coating film was visually confirmed to be cured before light irradiation by an LED lamp.

Accordingly, the photoreactive composition of Comparative Example 2 was cured by heating before light irradiation, and was problematic in terms of stability. It was presumed that the reason is because the photoreactive composition was heated, thereby resulting in a reaction of an amino group of Michler's ketone and an epoxy group of the base-reactive compound (9)-201.

Example 2

(Production of Photoreactive Composition)

The base-reactive compound (9)-201 (0.14 g), the following compound (1)-4A-101 (0.017 g, 7% by mol with respect to glycidyl methacrylate as a raw material of the base-reactive compound), 2-tert-butylanthracene (tBAnt, 100% by mol with respect to the compound (1)-4A-101) as a specified polycyclic aromatic compound, and chloroform (0.85 g) were blended, and stirred at 25° C. for 1 minute, thereby obtaining a photoreactive composition.

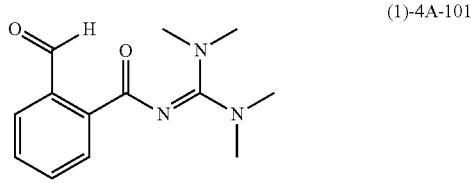 [SMILES: CN(C)C(=NC(=O)c1ccccc1C=O)N(C)C]

(1)-4A-101

(Production of Reaction Product)

A silicon wafer was coated with the photoreactive composition obtained above, according to a spin coating method in conditions of 1500 rpm and 30 seconds, and the thickness (the thickness of the coating film before light irradiation) of the resulting coating film was measured. The thickness of the coating film was 4 μm. Next, the coating film (photoreactive composition layer) was heated (pre-baked) at 70° C. for 2 minutes, and thereafter the coating film was irradiated with light at a wavelength of 365 nm in each condition of exposure doses of from 0 to 3000 mJ/cm$^2$ at an illuminance of 50 mW/cm$^2$ by use of an LED lamp.

Next, the coating film irradiated with light in each condition of exposure doses of from 0 to 3000 mJ/cm$^2$ was heated (post-baked) at 80° C. for 90 minutes. Such each coating film, except for that in an exposure dose of 0 mJ/cm$^2$, was tried to be finally formed into a reaction product obtained by polymerization of the base-reactive compound (9)-201.

Figure 4:
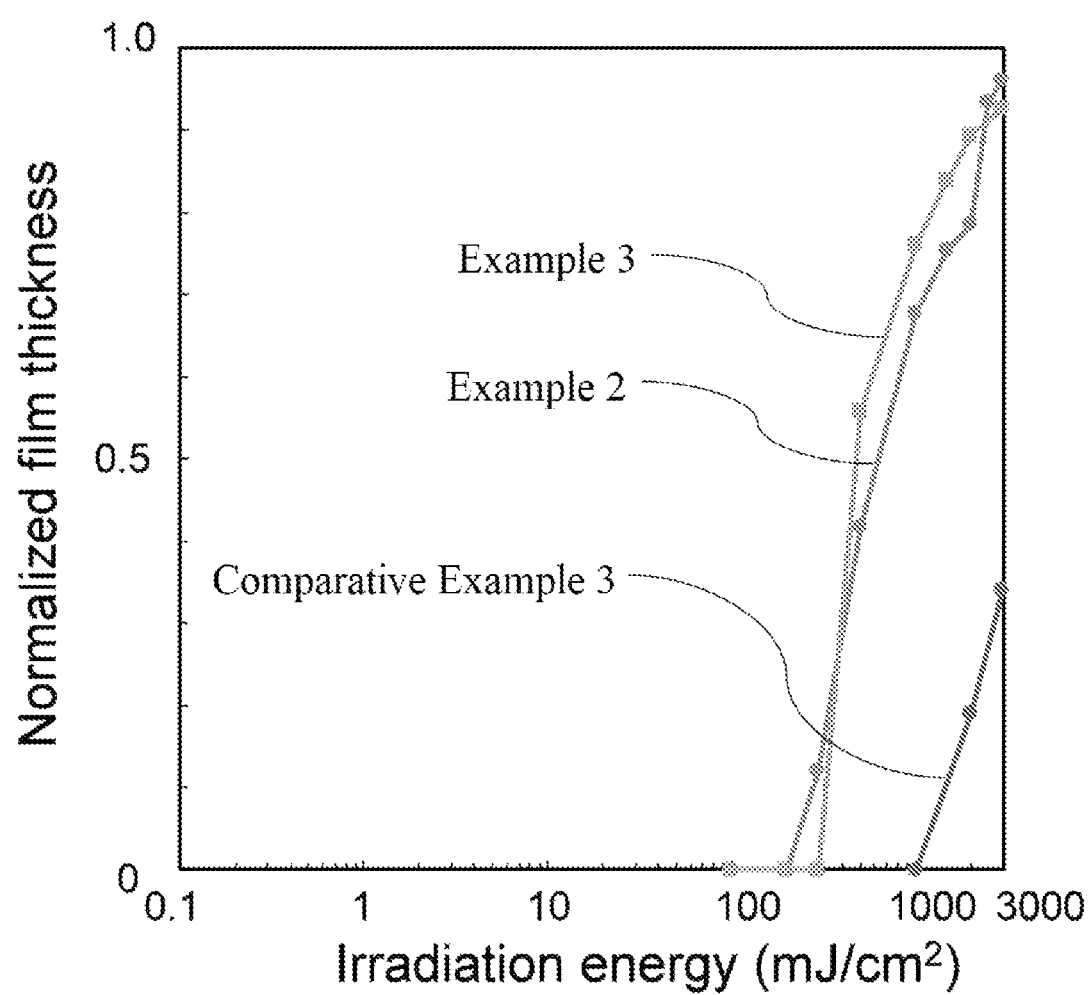
FIG. 4 is a graph illustrating the relationship between the exposure doses and the normalized remaining thickness of a coating film in Examples 2 and 3, and Comparative Example 3.

Next, such each coating film after post-baking was washed with chloroform, thereafter the thickness of such each coating film washed (thickness of coating film after post-baking) was measured, and the normalized remaining thickness of such each coating film was calculated according to Expression (ii) above. The results are illustrated in FIG. 4.

Example 3

A photoreactive composition was obtained in the same manner as in Example 2 except that the specified polycyclic aromatic compound in Example 2 was changed from 2-tert-butylanthracene (tBAnt, 100% by mol with respect to compound (1)-4A-101) to thioxanthone (TX, 100% by mol with respect to compound (1)-4A-101). A reaction product was produced in the same conditions as those in Example 2, and the normalized remaining thickness was calculated. The results are illustrated in FIG. 4.

Comparative Example 3

A photoreactive composition was obtained in the same manner as in Example 2 except that no specified polycyclic aromatic compound was used in Example 2, thereafter a reaction product was produced in the same conditions as those in Example 2, and the normalized remaining thickness was calculated. The results are illustrated in FIG. 4.

Example 4

(Production of Photoreactive Composition)

The base-reactive compound (9)-201 (0.14 g), the following compound (1)-5B-101 (0.015 g, 7% by mol with respect to glycidyl methacrylate as a raw material of the base-reactive compound), thioxanthone (TX, 100% by mol with respect to the compound (1)-5B-101) as a specified polycyclic aromatic compound, and chloroform (0.82 g) were blended, and stirred at 25° C. for 1 minute, thereby obtaining a photoreactive composition.

(Production of Reaction Product)

A silicon wafer was coated with the resulting photoreactive composition according to a spin coating method in conditions of 1500 rpm and 30 seconds, and the thickness (the thickness of the coating film before light irradiation) of the resulting coating film was measured. The thickness of the coating film was 4 μm. Next, the coating film (photoreactive composition layer) was heated (pre-baked) at 75° C. for 2 minutes, and thereafter the coating film was irradiated with light at a wavelength of 365 nm in each condition of exposure doses of from 0 to 10000 mJ/cm$^2$ at an illuminance of 50 mW/cm$^2$ by use of an LED lamp.

Next, the coating film irradiated with light in each condition of exposure doses of from 0 to 10000 mJ/cm$^2$ was heated (post-baked) at 100° C. for 90 minutes. The normalized remaining thickness was calculated in the same procedure as in Example 2. The results are illustrated in FIG. 5.

As illustrated in FIG. 4, Examples 2 and 3 each exhibited a high normalized remaining thickness in the same exposure doses, as compared with Comparative Example 3. The reason is because Examples 2 and 3 each exhibited a high generating efficiency of a base from the compound (1)-4A-101, as compared with Comparative Example 3, thus exhibited high reactivity of the base-reactive compound (9)-201 and a high production efficiency of a reaction product.

It was indicated from the foregoing that Examples 2 and 3 each exhibited excellent optical sensitivity of a photobase generator in the long-wavelength ultraviolet region.

Figure 5:
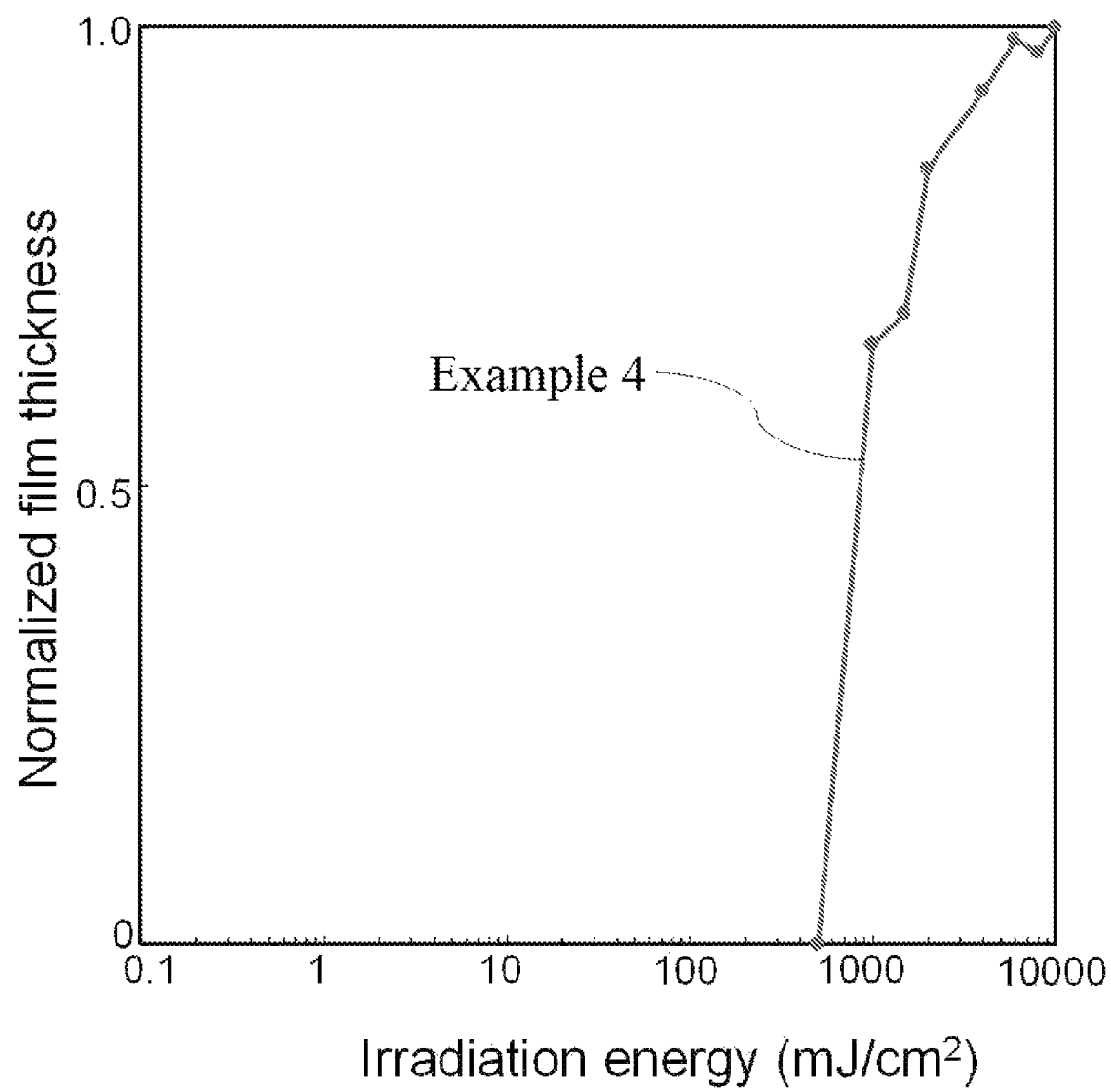
FIG. 5 is a graph illustrating the relationship between the exposure doses and the normalized remaining thickness of a coating film in Example 4.

It was further indicated that Example 4 also exhibited a high production efficiency of a reaction product and excellent optical sensitivity of a photobase generator in the long-wavelength ultraviolet region, in consideration of FIG. 4 and FIG. 5.

The disclosure of Japanese Patent Application No. 2018-089280 filed on May 7, 2018 is herein incorporated by reference in its entity.

All documents, patent applications, and technical standards described herein are herein incorporated by reference, as if each individual document, patent application, and technical standard were specifically and individually indicated to be incorporated by reference.

The invention claimed is:

1. A photoreactive composition, comprising:
    a base-reactive compound;
    a photobase generator that is represented by the following Formula (1) and that generates a base when irradiated with light; and
    at least one compound selected from the group consisting of a polycyclic aromatic compound having a fused ring structure having two or more rings, and a polycyclic aromatic compound having three or more aromatic rings and having a conjugated structure including any two or more of the three or more aromatic rings,
    wherein the base-reactive compound is a compound having two or more groups that will have their polarity converted by the action of a base and that exhibit reactivity, in one molecule, or a compound having two or more groups that will react under the action of a base, in one molecule:

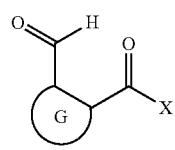

(1)

wherein, in Formula (1), G is a divalent aromatic group; and X is a group represented by the following Formula (1)-11, (1)-12, (1)-13, (1)-14, or (1)-15; and

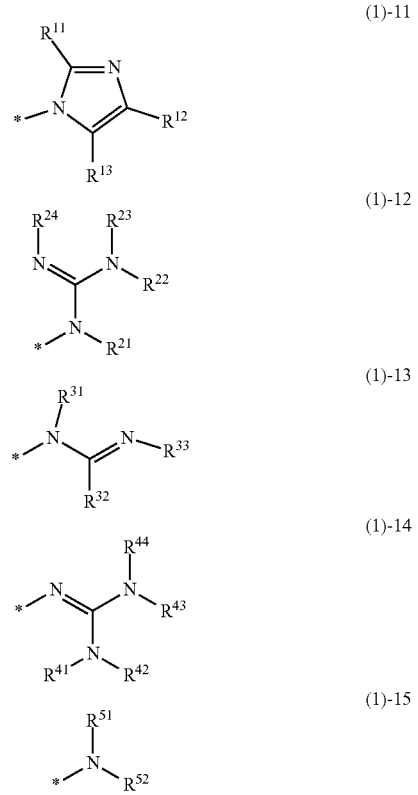

wherein, in Formula (1)-11 to Formula (1)-15, each of $R^{11}$, $R^{12}$, $R^{13}$, $R^{22}$, $R^{23}$, $R^{24}$, $R^{32}$, $R^{33}$, $R^{41}$, $R^{42}$, $R^{43}$, and $R^{44}$ independently represents a hydrogen atom or a hydrocarbon group; each of $R^{21}$, $R^{31}$, $R^{51}$, and $R^{52}$ independently represents a hydrocarbon group; in a case in which two or more of $R^{11}$, $R^{12}$, and $R^{13}$ are hydrocarbon groups, these hydrocarbon groups are optionally bound to each other to form a ring; in a case in which two or more of $R^{21}$, $R^{22}$, $R^{23}$, and $R^{24}$ are hydrocarbon groups, these hydrocarbon groups are optionally bound to each other to form a ring; in a case in which two or more of $R^{31}$, $R^{32}$, and $R^{33}$ are hydrocarbon groups, these hydrocarbon groups are optionally bound to each other to form a ring; in a case in which two or more of $R^{41}$, $R^{42}$, $R^{43}$, and $R^{44}$ are hydrocarbon groups, these hydrocarbon groups are optionally bound to each other to form a ring; $R^{51}$ and $R^{52}$ are optionally bound to each other to form a ring; and a bond marked with a symbol * is formed toward a carbon atom to which X is bound.

2. The photoreactive composition according to claim 1, wherein the polycyclic aromatic compound having a fused ring structure having two or more rings has three or more ring structures.

3. The photoreactive composition according to claim 1, wherein the polycyclic aromatic compound having a fused ring structure having two or more rings is at least one selected from the group consisting of anthraquinone, thioxanthone, anthracene, and any derivative thereof.

4. The photoreactive composition according to claim 1, wherein:
    the polycyclic aromatic compound having three or more aromatic rings and having a conjugated structure including any two or more of the three or more aromatic rings is a benzophenone derivative, and
    the benzophenone derivative is a compound in which at least one carbon atom included in an aromatic ring in a benzophenone skeleton is bound to the aromatic ring directly or via a divalent linking group.

5. A reaction product obtained by reacting the photoreactive composition according to claim 1.

6. A method of producing a reaction product, the method comprising:
    a step of irradiating the photoreactive composition according to claim 1 with light, thereby generating the base from the photobase generator.

7. The method of producing a reaction product according to claim 6, wherein the photoreactive composition is irradiated with light at a wavelength of 300 nm or more.

8. The photoreactive composition according to claim 2, wherein:
    the polycyclic aromatic compound having three or more aromatic rings and having a conjugated structure including any two or more of the three or more aromatic rings is a benzophenone derivative, and
    the benzophenone derivative is a compound in which at least one carbon atom included in an aromatic ring in a benzophenone skeleton is bound to the aromatic ring directly or via a divalent linking group.

9. The photoreactive composition according to claim 3, wherein:
    the polycyclic aromatic compound having three or more aromatic rings and having a conjugated structure including any two or more of the three or more aromatic rings is a benzophenone derivative, and
    the benzophenone derivative is a compound in which at least one carbon atom included in an aromatic ring in a benzophenone skeleton is bound to the aromatic ring directly or via a divalent linking group.

10. A reaction product obtained by reacting the photoreactive composition according to claim 2.

11. A reaction product obtained by reacting the photoreactive composition according to claim 3.

12. A reaction product obtained by reacting the photoreactive composition according to claim 4.

13. A reaction product obtained by reacting the photoreactive composition according to claim 8.

14. A reaction product obtained by reacting the photoreactive composition according to claim 9.

15. A method of producing a reaction product, the method comprising:
    irradiating the photoreactive composition according to claim 2 with light, thereby generating the base from the photobase generator.

16. A method of producing a reaction product, the method comprising:
    irradiating the photoreactive composition according to claim 3 with light, thereby generating the base from the photobase generator.

17. A method of producing a reaction product, the method comprising:
    irradiating the photoreactive composition according to claim 4 with light, thereby generating the base from the photobase generator.

18. A method of producing a reaction product, the method comprising:
    irradiating the photoreactive composition according to claim 8 with light, thereby generating the base from the photobase generator.

19. A method of producing a reaction product, the method comprising:
    irradiating the photoreactive composition according to claim 9 with light, thereby generating the base from the photobase generator.

20. The method of producing a reaction product according to claim 15, wherein the photoreactive composition is irradiated with light at a wavelength of 300 nm or more.

\* \* \* \* \*